United States Patent [19]

Horstmann et al.

[11] 4,076,943
[45] Feb. 28, 1978

[54] 1-SUBSTITUTED-3-AMINO-PYRAZOL-5-ONES

[75] Inventors: Harald Horstmann; Karl Meng, both of Wuppertal; Egbert Wehinger, Neviges, all of Germany

[73] Assignee: Bayer Aktiengesellschaft, Germany

[21] Appl. No.: 756,179

[22] Filed: Jan. 3, 1977

Related U.S. Application Data

[60] Division of Ser. No. 521,906, Nov. 7, 1974, abandoned, which is a continuation of Ser. No. 371,959, Jun. 21, 1973, abandoned.

[30] Foreign Application Priority Data

Jun. 23, 1972 Germany .............................. 2230792
Jun. 23, 1972 Germany .............................. 2230675

[51] Int. Cl.$^2$ ........................................... C07D 231/52
[52] U.S. Cl. .............................. 548/360; 260/340.5 R; 424/273 P
[58] Field of Search ........................................ 548/360

[56] References Cited

U.S. PATENT DOCUMENTS 3,823,156  7/1974  Oku et al. ..................... 260/310 A

OTHER PUBLICATIONS

Gagnon et al., Chem. Abs., vol. 47, 1953, 6940.

Primary Examiner—Natalie Trousof
Assistant Examiner—Jane T. Fan
Attorney, Agent, or Firm—Jacobs & Jacobs

[57] ABSTRACT

1-Substituted-3-amino-pyrazol-5-ones of the formula

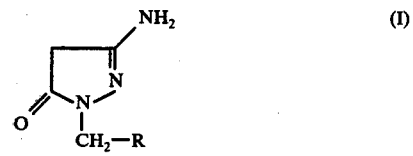

or a pharmaceutically acceptable non-toxic salt thereof wherein R is a substituted phenyl or naphthyl group or unsubstituted β-naphthyl, anthryl or phenanthryl which exhibit strong diuretic, saluretic and anti-hypertensive effects.

4 Claims, No Drawings

1-SUBSTITUTED-3-AMINO-PYRAZOL-5-ONES

CROSS-REFERENCE

This is a division of Ser. No. 521,906 filed Nov. 7, 1974 which is a continuation of Ser. No. 371,959, filed June 21, 1973 both now abandoned.

The present invention relates to 1-substituted-3-amino-pyrazol-5-ones, a process for their production, pharmaceutical compositions embodying said compounds as the active agent and methods of rendering diuretic and saluretic therapy to humans and animals and a method of treating hypertension in humans and animals.

More particularly, the compounds of the present invention are 1-aryl-3-amino-pyrazol-5-ones. Certain 1-aryl-3-amino-pyrazol-5-ones have been disclosed as color-coupling agents for color photography (A. Weissberger et al., J. Am. Chem. Soc. 64, 2133 (1942)).

Certain 3-amino-pyrazol-5-ones are also known as intermediates for the production of color-coupling agents (British Pat. No. 599,919; U.S. Pat. No. 2,367,523; U.S. Pat. No. 2,376,380, U.S. Pat. No. 2,511,231; U.S. Pat. No. 2,600,788, U.S. Pat. No. 2,619,419; U.S. Pat. No. 2,672,417).

The present invention comprises 1-aryl-3-amino-pyrazol-5-ones of the formula

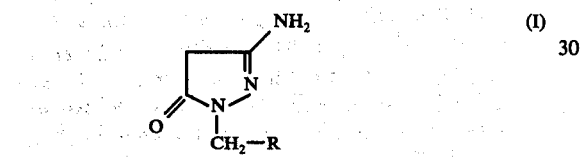

or a pharmaceutically acceptable non-toxic salt thereof wherein R is (a) phenyl substituted by one or two identical or different substituents selected from the group consisting of alkyl preferably of 1 to 8 carbon atoms and especially 1 to 4 carbon atoms, phenyl, trifluoromethyl, trifluoromethoxy, nitro, cyano, fluoro, bromo, iodo, alkylamino, especially lower alkylamino, a carbonamido moiety of the formula

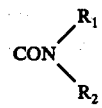

and a sulphonamido moiety of the formula

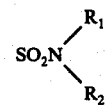

wherein $R_1$ and $R_2$ are each hydrogen or straight or branched chain alkyl, especially of 1 to 4 carbon atoms, or $R_1$ and $R_2$ together with the nitrogen atom to which they are attached may be linked together to form a 5-, 6- or 7-membered heterocyclic ring wherein the nitrogen atom is the only heteroatom or wherein oxygen is also present as a ring member;

(b) phenyl having an annellated branched or unbranched, saturated or unsaturated, 5-, 6- or 7-membered isocyclic or heterocyclic ring wherein the heterocyclic ring has one or more oxygen heteroatoms and/or one or more sulphur heteroatoms, said phenyl ring being otherwise unsubstituted or chloro-substituted;

(c) phenyl substituted by $SO_n$— alkyl, especially straight or branched chain alkyl of 1 to 4 carbon atoms, wherein $n$ is zero, 1 or 2, alkoxy, especially straight or branched chain alkoxy of 2 to 4 carbon atoms or $-O-(CH_2)_{n'}-N(alkyl)_2$ wherein the alkyl groups contain a total of 2 to 4 carbon atoms and $n'$ is 2 or 3;

(d) phenyl substituted by 2 identical substituents selected from the group consisting of alkoxy, especially of 1 to 4 carbon atoms, and trifluoromethyl;

(e) phenyl having 2 different substituents selected from the group consisting of alkyl, particularly of 1 to 8 carbon atoms, and especially 1 to 4 carbon atoms, phenyl, halogen (fluoro, choloro, bromo or iodo), alkoxy, particularly of 1 to 8 carbon atoms and especially 1 to 4 carbon atoms, trifluoromethyl, trifluoromethoxy, alkylamino, especially lower alkylamino, nitro, cyano, — $SO_n$— alkyl, especially of 1 to 4 carbon atoms wherein $n$ is zero, 1 or 2, a carbonamido moiety of the formula

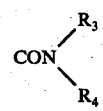

and a sulphonamido moiety of the formula

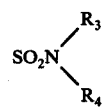

wherein $R_3$ and $R_4$ are each hydrogen or alkyl, especially of 1 to 4 carbon atoms;

(f) trichlorophenyl;

(g) naphthyl having 1 or 2 identical or different substituents, preferably identical, selected from the group consisting of halogen (fluoro, chloro, bromo or iodo) and alkyl, especially of 1 to 4 carbon atoms; or (h) unsubstituted α-naphthyl, anthryl or phenanthryl.

These compounds are useful as diuretics, saluretics, and anti-hypertensive agents.

Formula I is only one of a number of tautomeric structures that can be assumed by the compounds of the present invention. While Formula I represents a preferred structure, the present invention embraces all of the tautomeric forms of the compounds of the present invention including the salts, whether present singly or as a mixture of two or more tautomeric forms.

The other tautomeric structures are represented by the following:

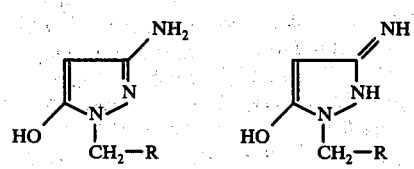

-continued

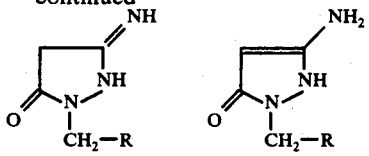

The present invention also includes a process for the production of the 1-substituted-3-amino-pyrazol-5-ones which comprises reacting a hydrazine of the formula

R—CH₂—NH—NH₂      (II)

wherein R is as above defined with an acetic acid derivative of the formula

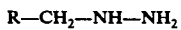
$$\begin{array}{c}Y'\\ \phantom{x}\diagdown\\ \phantom{xx}CH-COX\\ \phantom{x}\diagup\\ Y''\end{array}$$      (III)

wherein X is hydroxy, alkoxy, preferably lower alkoxy, aralkoxy, preferably having 6 to 10 carbon atoms in the aryl moiety and wherein the alkoxy moiety is preferably a lower alkoxy moiety, amino or alkylamino, preferably lower alkylamino; and either
(a) Y' is hydrogen and Y'' is cyano; or
(b) Y' and Y'' together represent the group

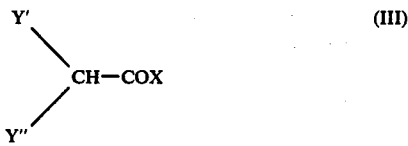

wherein Y is alkoxy, preferably lower alkoxy, aryloxy, preferably of 6 to 10 carbon atoms in the aryl moiety, aralkoxy, preferably of 6 to 10 carbon atoms in the aryl moiety and wherein the alkoxy moiety is preferably lower alkoxy, alkylmercapto, preferably lower alkylmercapto, aralkylmercapto, preferably of 6 to 10 carbon atoms in the aryl moiety and wherein the alkyl moiety is preferably lower alkyl or amino.

During the course of the reaction of the hydrazine with the acetic acid derivative, an amidrazone of the formula

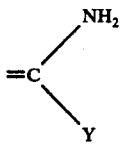      (IV)

wherein R is as above defined, is formed as an intermediate. This amidrazone may be isolated and then cyclized thermally or in the presence of a basic condensation catalyst. Alternatively, the reaction of the hydrazine with the acetic acid derivative may be carried out in a single stage.

Depending on the nature of the starting substances used, the synthesis of the compounds according to the invention can be represented by one of the following reaction schemes, with 3-amino-1-(p-bromobenzyl)-pyrazol-5-one being shown by way of example and the intermediate amidrazone (Formula (IV)) not being shown:

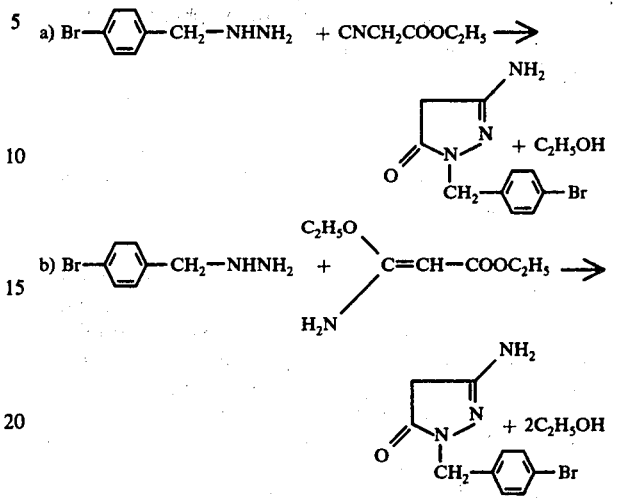

According to a preferred embodiment of the present invention, R is preferably either
(a) phenyl substituted by one or two identical or different substituents selected from the group consisting of alkyl of 1 to 8 carbon atoms, phenyl, trifluoromethyl, trifluoromethoxy, nitro, cyano, fluoro, bromo and iodo;
(b) phenyl having an annellated branched or unbranched, saturated or unsaturated, 5-, 6- or 7-membered isocyclic or heterocyclic ring wherein said heterocyclic ring has a sulphur heteroatom, sulphur heteroatom and an oxygen heteroatom or a sulphur heteroatom and two oxygen heteroatoms;
(c) phenyl substituted by straight or branched chain alkoxy of 2 to 4 carbon atoms;
(d) phenyl substituted by 2 identical substituents selected from the group consisting of alkoxy of 1 to 4 carbon atoms and trifluoromethyl;
(e) phenyl having 2 different substituents selected from the group consisting of alkyl of 1 to 8 carbon atoms, phenyl, halogen, alkoxy of 1 to 8 carbon atoms, trifluoromethyl, trifluoromethoxy, nitro and cyano;
(f) trichlorophenyl;
(g) naphthyl having 1 or 2 identical substituents selected from the group consisting of halogen and alkyl of 1 to 4 carbon atoms; or
(h) β-naphthyl.

According to another embodiment of the present invention, R is
(a) phenyl substituted by one or two identical or different substituents selected from the group consisting of alkyl of 1 to 8 carbon atoms, phenyl, trifluoromethoxy, nitro, fluoro, bromo and iodo;
(b) phenyl having an annellated branched or unbranched, saturated or unsaturated, 5-, 6- or 7-membered isocyclic or heterocyclic ring wherein said heterocyclic ring has a sulphur heteroatom, sulphur heteroatom and an oxygen heteroatom or a sulphur heteroatom and two oxygen heteroatoms;
(c) phenyl substituted by straight or branched chain alkoxy of 2 to 4 carbon atoms;

(d) phenyl substituted by 2 identical substituents selected from the group consisting of alkoxy of 1 to 4 carbon atoms and trifluoromethyl;
(e) phenyl having 2 different substituents selected from the group consisting of alkyl of 1 to 8 carbon atoms, phenyl, halogen, alkoxy of 1 to 8 carbon atoms, trifluoromethyl, trifluoromethoxy, nitro and cyano;
(f) trichlorophenyl;
(g) naphthyl having 1 to 2 identical substituents selected from the group consisting of halogen and alkyl of 1 to 4 carbon atoms; or
(h) β-naphthyl.

The hydrazines of Formula II used as starting materials are known from the literature or can be produced according to methods known from the literature (compare, for example, HOUBEN-WEYL, "Methoden der organischen Chemie (Methods of Organic Chemistry), volume X, 2, page 6).

Representative hydrazines useful in producing the compounds of the present invention include:
2-methylbenzylhydrazine,
3-methylbenzylhydrazine,
4-methylbenzylhydrazine,
3-ethylbenzylhydrazine,
4-ethylbenzylhydrazine,
3-n-propylbenzylhydrazine,
4-n-propylbenzylhydrazine,
4-isopropylbenzylhydrazine,
4-n-butylbenzylhydrazine,
4-tert.-butylbenzylhydrazine,
4-isobutylbenzylhydrazine,
4-phenylbenzylhydrazine,
2-phenylbenzylhydrazine,
4-cyclopentylbenzylhydrazine,
4-cyclohexylbenzylhydrazine,
3,4-dimethylbenzylhydrazine,
2,5-dimethylbenzylhydrazine,
2,4-dimethylbenzylhydrazine,
3,4-dimethylbenzylhydrazine,
3-methyl-4-propylbenzylhydrazine,
2-fluorobenzylhydrazine,
3-fluorobenzylhydrazine,
4-fluorobenzylhydrazine,
2-bromobenzylhydrazine,
3-bromobenzylhydrazine,
4-bromobenzylhydrazine,
3-iodobenzylhydrazine,
4-iodobenzylhydrazine,
2-nitrobenzylhydrazine,
3-nitrobenzylhydrazine,
4-nitrobenzylhydrazine,
3-cyanobenzylhydrazine,
4-cyanobenzylhydrazine,
3-trifluoromethoxybenzylhydrazine,
4-trifluoromethoxybenzylhydrazine,
3-carbonamidobenzylhydrazine,
4-dimethylaminocarbonylbenzylhydrazine,
4-sulphonamidobenzylhydrazine,
4-dimethylsulphonamidobenzylhydrazine,
4-dimethylaminobenzylhydrazine,
4-methylmercaptobenzylhydrazine,
4-ethylmercaptobenzylhydrazine,
4-ethylsulphonylbenzylhydrazine,
3-butoxybenzylhydrazine,
4-butoxybenzylhydrazine,
3-ethoxybenzylhydrazine,
3-(β-diethylaminoethoxy)-benzylhydrazine,
3,4-dimethoxybenzylhydrazine,
3,4-methylenedioxybenzylhydrazine,
3,5-dimethoxybenzylhydrazine,
3,5-diethoxybenzylhydrazine,
3,4-bis-trifluoromethylbenzylhydrazine,
3-chloro-4-methylbenzylhydrazine,
4-chloro-3-methylbenzylhydrazine,
3-cyano-4-methylbenzylhydrazine,
3-methyl-4-nitrobenzylhydrazine,
4-trifluoromethyl-3-methylbenzylhydrazine,
3-trifluoromethyl-4-methylbenzylhydrazine,
4-chloro-3-trifluoromethylbenzylhydrazine,
4-trifluoromethyl-3-chlorobenzyllhydrazine,
4-chloro-3-bromobenzylhydrazine,
4-bromo-3-chlorobenzylhydrazine,
3,4-dibromobenzylhydrazine,
2-fluoro-5-chlorobenzylhydrazine,
2-fluoro-5-chlorobenzylhydrazine,
2-chloro-4-fluorobenzylhydrazine,
4-chloro-3-sulphonamidobenzylhydrazine,
4-chloro-3-methoxybenzylhydrazine,
4-chloro-3-butoxybenzylhydrazine,
2-nitro-4-di-methylaminobenzylhydrazine,
2,4,5-trichlorobenzylhydrazine,
5-hydrazinomethylindane,
2-hydrazinomethylnaphthalene,
2-hydrazinomethyl-5,6,7,8-tetrahydronaphthalene,
2-hydrazinomethyl-5-methylnaphthalene,
2-hydrazinomethyl-5-chloronaphthalene,
2-hydrazinomethyl-8-chloronaphthalene,
2-hydrazinomethylanthracene and
3-hydrazinomethylphenanthrene.

According to a preferred embodiment of the present invention, the acetic acid derivative may be represented by the formula

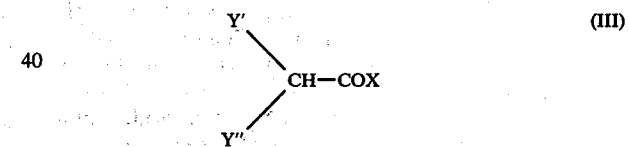 (III)

wherein X is hydroxy, alkoxy of 1 to 6 carbon atoms, especially branched chain alkoxy of 3 to 6 carbon atoms, benzyloxy, amino or alkylamino or dialkylamino of 1 to 4 carbon atoms in each alkyl moiety; and either
(a) Y' is hydrogen and Y" is cyano;
or
(b) Y' and Y" together are the group

wherein Y is alkoxy of 1 to 6 carbon atoms, alkylmercapto of 1 to 6 carbon atoms in the alkyl moiety, benzyloxy, phenoxy, benzylmercapto or amino.

The acetic acid derivatives according to Formula III used as starting compounds are known from the literature or can be produced by processes known from the literature [see (a) Org. Synth., Coll. I, 249 or Org. Synth. 41, 50 and (b) Cope, J. Am. Chem. Soc. 67, 1047 (1945)].

According to whether Y' and Y" have the meanings given above at (a) or at (b), the acetic acid derivative of Formula III is either (a) a cyanoacetic acid ester or amide of (b) a β-substituted β-amino-acrylic acid ester or amide.

Representative compounds of Formula III are:
(a) Cyanoacetic acid esters and amides:
cyanoacetic acid methyl ester,
cyanoacetic acid ethyl ester,
cyanoacetic acid propyl ester,
cyanoacetic acid isopropyl ester,
cyanoacetic acid n-butyl ester (compare Org. Synth. 41, page 5),
cyanoacetic acid isobutyl ester,
cyanoacetic acid tert.butyl ester,
cyanoacetic acid hexyl ester,
cyanoacetic acid benzyl ester,
cyanoacetic acid amide,
cyanoacetic acid methylamide,
cyanoacetic acid diethylamide and
cyanoacetic acid butylamide.

(b) β-substituted β-aminoacrylic acid esters and amides:
β-amino-β-methoxyacrylic acid ethyl ester,
β-amino-β-ethoxyacrylic acid ethyl ester,
β-amino-β-butoxyacrylic acid butyl ester,
β-amino-β-phenoxyacrylic acid ethyl ester,
β-amino-β-benzyloxyacrylic acid benzyl ester,
β-amino-β-ethoxyacrylic acid amide,
β-amino-β-ethoxyacrylic acid diethylamide,
β-amino-β-methylmercaptoacrylic acid ethyl ester,
β-amino-β-benzylmercaptoacrylic acid ethyl ester,
β-amino-β-methylmercaptoacrylic acid amide,
β,β-diaminoacrylic acid ethyl ester and
β,β-diaminoacrylic acid amide.

The process of the present invention can, if desired, be carried out in the presence of an inert diluent and basic or acidic catalysts.

Suitable diluents are all inert organic solvents which, when they are miscible with water, can if desired be diluted with water. Preferred solvents include hydrocarbons (such as benzene, toluene and xylene), halogenated hydrocarbons (such as methylene chloride, chloroform, carbon tetrachloride and chlorobenzene), alcohols (such as methanol, ethanol, propanol, butanol, benzyl alcohol and glycol monomethyl ether), ethers (such as tetrahydrofurane, dioxane and glycol dimethyl ether), amides (such as dimethylformamide, dimethylacetamide, N-methylpyrrolidone and hexamethylphosphoric acid triamide), sulphoxides (such as dimethylsulphoxide), sulphones (such as sulpholane) and tertiary bases (such as pyridine, picoline, collidine, lutidine and quinoline).

As basic condensation agents, inorganic and organic bases may be used. Preferred agents include alkali metal hydroxides (such as sodium hydroxide), potassium carbonates, and alcoholates (such as sodium alcoholate).

As acid catalysts, inorganic and organic acids may be used. Preferred catalysts include hydrogen halides, sulphuric acid and sulphonic acids (such as p-toluenesulphonic acid and trifluoromethylsulphonic acid).

The reaction temperatures can be varied over a substantial range. In general, the reaction is carried out at between 10° and 200° C, preferably between 20° and 100° C. It is carried out under normal pressure but it can also be carried out in closed vessels at higher pressure.

In carrying out the process (a) according to the invention (when the acetic acid derivative is a cyanoacetic acid ester or amide) one mol of the cyanoacetic acid derivative of Formula III and 1–3 mols, preferably 2 mols, of a basic condensation agent are preferably employed per one mol of the hydrazine of Formula II. According to this process, salts of the 1-aryl-3-aminopyrazol-5-ones of Formula I are obtained and the free 3-amino-pyrazol-5-ones can be liberated when required by treatment of the salt with equivalent amounts of a dilute acid. They can easily be purified by recrystallisation from a suitable solvent or by dissolving in dilute sodium hydroxide solution, filtration in the presence of animal charcoal and reprecipitation by means of dilute acids.

In carrying out the process (b) according to the invention (when the actic acid derivative of Formula III is a β-substituted β-amino-acrylic acid ester or amide) one mol of the hydrazine of Formula II and one mol of the acetic acid derivative of Formula III (β-aminoacrylic acid derivative) are preferably reacted. Here it is possible to start either from the β-aminoacrylic acid derivative (III) in the free form or from one of its acid addition salts. In the latter case, one mol of a base is appropriately added in order to liberate the β-aminoacrylic acid derivative. If the hydrazine derivative and the β-aminoacrylic acid derivative are used in the free form, it is advisable to add 1 – 10% of an acid catalyst. Another possible procedure is to add an appropriately smaller amount of a base to the reaction mixture for neutralising the salt of the aminoacrylic acid derivative.

The reaction can be directed in such a way that first an amidrazone (IV) is produced, and that this is then cyclized to give the desired compound according to the invention in a second reaction step, thermally or by the action of a basic condensation agent. However, the one-stage synthesis is particularly advantageous.

The following compounds are representative of the 1-aryl-3-amino-pyrazol-5-ones of the present invention:
3-amino-1-(3,4,5-trichlorobenzyl)-pyrazol-5-one,
3-amino-1-(4-fluorobenzyl)-pyrazol-5-one,
3-amino-1-(4-bromobenzyl)-pyrazol-(5)-one,
3-amino-1-(4-chloro-3-bromobenzyl)-pyrazol-5-one,
3-amino-1-(4-fluoro-3-chlorobenzyl)-pyrazol-5-one,
3-amino-1-(3,4-dibromobenzyl)-pyrazol-5-one,
3-amino-1-(4-bromo-3-chlorobenzyl)-pyrazol-5-one,
3-amino-1-(4-fluoro-3-bromobenzyl)-pyrazol-5-one,
3-amino-1-(4-methylbenzyl)-pyrazol-5-one,
3-amino-1-(4-methyl-3-chlorobenzyl)-pyrazol-5-one,
3-amino-1-(4-ethylbenzyl)-pyrazol-5-one,
3-amino-1-(4-chloro-3-methylbenzyl)-pyrazol-5-one,
3-amino-1-(4-fluoro-3-methylbenzyl)-pyrazol-5-one,
3-amino-1-(4-t.-butylbenzyl)-pyrazol-5-one,
3-amino-1-(2-chloro-3-methylbenzyl)-pyrazol-5-one,
3-amino-1-(3-chloro-5-methylbenzyl)-pyrazol-5-one,
3-amino-1-(3-bromo-5-methylbenzyl)-pyrazol-5-one,
3-amino-1-(3,5-dimethylbenzyl)-pyrazol-5-one,
3-amino-1-(4-propyl-3-chlorobenzyl)-pyrazol-5-one,
3-amino-1-(4-bromo-3-methylbenzyl)-pyrazol-5-one,
3-amino-1-(4-phenylbenzyl)-pyrazol-5-one,
3-amino-1-(3-phenylbenzyl)-pyrazol-5-one,
3-amino-1-(3-phenyl-4-chlorobenzyl)-pyrazol-5-one,
3-amino-1-(4-phenyl-3-methylbenzyl)-pyrazol-5-one,
3-amino-1-(4-chloro-3-trifluoromethylbenzyl)-pyrazol-5-one,
3-amino-1-(3-chloro-4-trifluoromethylbenzyl)-pyrazol-5-one,
3-amino-1-(4-fluoro-3-trifluoromethylbenzyl)-pyrazol-5-one,
3-amino-1-(4-bromo-3-trifluoromethylbenzyl)-pyrazol-5-one, 3-amino-1-(3-chloro-5-trifluoromethylbenzyl)-pyrazol-5-one,
3-amino-1-(4-trifluoromethyl-3-methylbenzyl)-pyrazol-5-one,
3-amino-1-(4-methyl-3-trifluoromethylbenzyl)-pyrazol-5-one,
3-amino-1-(3,4-dimethylbenzyl)-pyrazol-5-one,
3-amino-1-(2,5-dimethylbenzyl)-pyrazol-5-one,
3-amino-1-(3,4-trimethylenebenzyl)-pyrazol-5-one,
3-amino-1-(3,4-tetramethylenebenzyl)-pyrazol-5-one,
3-amino-1-(3,4-tetramethylene-5-chlorobenzyl)-pyrazol-5-one,
3-amino-1-(3,4-dimethoxybenzyl)-pyrazol-5-one,
3-amino-1-(3,4-methylenedioxybenzyl)-pyrazol-5-one,
3-amino-1-(3-chloro-4-methoxybenzyl)-pyrazol-5-one,
3-amino-1-(4-chloro-3-methoxybenzyl)-pyrazol-5-one,
3-amino-1-(4-methyl-3-methoxybenzyl)-pyrazol-5-one,
3-amino-1-(4-methoxy-3-methylbenzyl)-pyrazol-5-one,
3-amino-1-(4-nitrobenzyl)-pyrazol-5-one,
3-amino-1-(2-nitrobenzyl)-pyrazol-5-one,
3-amino-1-(4-nitro-3-methylbenzyl)-pyrazol-5-one,
3-amino-1-(3-nitro-4-methoxybenzyl)-pyrazol-5-one,
3-amino-1-(3-nitrobenzyl)-pyrazol-5-one,
3-amino-1-(2-methoxy-6-methylbenzyl)-pyrazol-5-one,
3-amino-1-(2-methoxy-6-chlorobenzyl)-pyrazol-5-one,
3-amino-1-(2-nitro-6-methylbenzyl)-pyrazol-5-one,
3-amino-1-(3-cyano-4-chlorobenzyl)-pyrazol-5-one,
3-amino-1-(4-cyano-3-methylbenzyl)-pyrazol-5-one,
3-amino-1-(4-cyano-3-methoxybenzyl)-pyrazol-5-one,
3-amino-1-(4-sulphonamidobenzyl)-pyrazol-5-one,
3-amino-1-(4-N,N-dimethylsulphonamidobenzyl)-pyrazol-5-one,
3-amino-1-(4-carbonamido-benzyl)-pyrazol-5-one,
3-amino-1-(4-N,N-dimethylcarbonamidobenzyl)-pyrazol-5-one,
3-amino-1-(3-N,N-dimethylcarbonamidobenzyl)-pyrazol-5-one,
3-amino-1-(naphthyl-(2)-methyl)-pyrazol-5-one,
3-amino-1-(1-methyl-naphthyl-(2)-methyl)-pyrazol-5-one,
3-amino-1-(3-chloro-naphthyl-(2)-methyl)-pyrazol-5-one,
3-amino-1-(4-methylsulphonyl-3-chlorobenzyl)-pyrazol-5-one,
3-amino-1-(3-methylsulphonyl-4-chlorobenzyl)-pyrazol-5-one,
3-amino-1-(3-methylsulphonyl-4-methylbenzyl)-pyrazol-5-one,
3-amino-1-(4-methylsulphonyl-3-methylbenzyl)-pyrazol-5-one,
3-amino-1-(4-sulphonamido-3-chlorobenzyl)-pyrazol-5-one,
3-amino-1-(5,6-dichloro-naphthylmethyl-2)-pyrazol-5-one,
3-amino-1-(6,8-dichloro-naphthylmethyl-2)-pyrazol-5-one,
3-amino-1-(5-chloro-naphthylmethyl-2)-pyrazol-5-one,
3-amino-1-(4-methylsulphonyl-3-bromobenzyl)-pyrazol-5-one,
3-amino-1-(4-trifluoromethoxybenzyl)-pyrazol-5-one,
3-amino-1-(3-trifluoromethoxybenzyl)-pyrazol-5-one and
3-amino-1-(4-trifluoromethoxy-3-chlorobenzyl)-pyrazol-5-one.

As mentioned above, the compounds of the present invention are useful for their diuretic and saluretic activity and for their anti-hypertensive effect. Upon oral or parenteral administration, the compounds of the present invention cause a large increase in the excretion of water and salt and are therefore useful for the treatment of edematous and hypertonic conditions. In addition, the compounds are useful in the treatment of acute renal failure.

The present invention also comprises a pharmaceutical composition which comprises a diuretically effective amount, a saluretically effective amount, or an anti-hypertensive amount of a compound of the formula

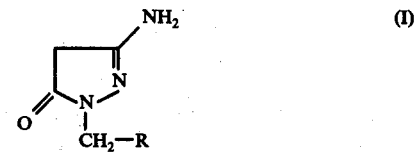

or a pharmaceutically acceptable non-toxic salt thereof, wherein R is aryl which is either unsubstituted or substituted by (a) 1, 2 or 3 identical or different substituents selected from the group consisting of halogen, alkyl of 1 to 8 carbon atoms, alkoxy of 1 to 8 carbon atoms, alkenoxy of 2 to 6 carbon atoms, cycloalkyl of 5 to 7 carbon atoms, trifluoromethyl, trifluoromethoxy and phenyl;

(b) 1 or 2 identical or different substituents selected from the group consisting of nitro, cyano, lower alkylamino of 1 to 4 carbon atoms, a carbonamido moiety of the formula

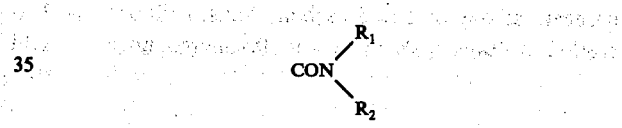

and a sulphonamido moiety of the formula $$SO_2N\begin{matrix}R_1\\R_2\end{matrix}$$

wherein $R_1$ and $R_2$ are each hydrogen or straight or branched chain alkyl of 1 to 4 carbon atoms, or $R_1$ and $R_2$ together with the nitrogen atom to which they are attached are linked together to form a 5-, 6- or 7-membered heterocyclic ring wherein the nitrogen atom is the only heteroatom or wherein oxygen is also present as a ring member;

(c) 1 substituent selected from the group consisting of dialkylamino of 1 to 4 carbon atoms in each alkyl moiety, and $SO_n$-alkyl of 1 to 4 carbon atoms wherein $n$ is zero, 1 or 2;

(d) 1 substituent selected from the group consisting of a moiety of the formula $$N\begin{matrix}R_1\\R_2\end{matrix}$$

wherein $R_1$ and $R_2$ are as above defined, nitro, cyano, a carbonamido moiety of the formula

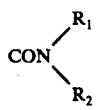

wherein $R_1$ and $R_2$ are as above defined, a sulphonamido moiety of the formula

wherein $R_1$ and $R_2$ are as above defined and $SO_n$-alkyl of 1 to 4 carbon atoms wherein $n$ is zero, 1 or 2, and 1 or 2 substituents selected from the group consisting of alkyl of 1 to 8 carbon atoms, alkoxy of 1 to 6 carbon atoms, halogen and trifluoromethyl;

(e) an annellated branched or unbranched, saturated or unsaturated, 5-, 6- or 7-membered isocyclic or heterocyclic ring having 1 or more heteroatoms selected from the group consisting of oxygen and sulphur and wherein said aryl moiety is either unsubstituted or chlorosubstituted;

(f) —O— $(CH_2)_{n'}$—$N(alkyl)_2$ wherein the alkyl groups contain a total of 2 to 4 carbon atoms and $n'$ is 2 or 3; or (g) 2 different substituents selected from the group consisting of alkyl of 1 to 8 carbon atoms, phenyl, halogen, alkoxy of 1 to 8 carbon atoms, trifluoromethyl, trifluoromethoxy, lower alkylamino, nitro, cyano, $SO_n$—alkyl of 1 to 4 carbon atoms wherein $n$ is zero, 1 or 2, a carbonamido moiety of the formula

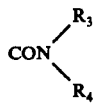

and a sulphonamido moiety of the formula

wherein $R_3$ and $R_4$ are each hydrogen or alkyl of 1 to 4 carbon atoms, in combination with a pharmaceutically acceptable nontoxic inert diluent or carrier.

According to one embodiment, R is aryl which is either unsubstituted or substituted by (a) 1, 2 or 3 identical or different substituents selected from the group consisting of halogen, trifluoromethyl, trifluoromethoxy, alkyl of 1 to 8 carbon atoms, alkoxy of 1 to 6 carbon atoms, alkenoxy of 2 to 6 carbon atoms, cycloalkyl of 5 to 7 carbon atoms and phenyl;

(b) 1 substituent selected from the group consisting of a moiety of the formula

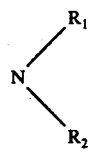

wherein $R_1$ and $R_2$ are each hydrogen or straight or branched chain alkyl of 1 to 4 carbon atoms, or $R_1$ and $R_2$ together with the nitrogen atom to which they are attached are linked together to form a 5-, 6- or 7-membered heterocyclic ring wherein the nitrogen atom is the only heteroatom or wherein oxygen is also present as a ring member, trifluoromethoxy, nitro, cyano, a carbonamido moiety of the formula

wherein $R_1$ and $R_2$ are as above defined, a sulphonamido moiety of the formula

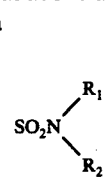

wherein $R_1$ and $R_2$ are as above defined and $SO_n$-alkyl of 1 to 4 carbon atoms wherein $n$ is zero, 1 or 2, or by 1 of said substituents and 1 or 2 substituents selected from the group consisting of alkyl of 1 to 8 carbon atoms, alkoxy of 1 to 6 carbon atoms, halogen and trifluoromethyl; or (c) an annellated branched or unbranched, saturated or unsaturated, 5-, 6- or 7-membered isocyclic or heterocyclic ring having up to 4 heteroatoms selected from the group consisting of 1 or 2 oxygen atoms and 1 or 2 sulphur atoms, and wherein said aryl moiety is either unsubstituted or chloro-substituted.

According to another embodiment, R is anthryl or phenanthryl; or phenyl or naphthyl substituted by (a) a member selected from the group consisting of 1, 2 or 3 alkyl moieties of 1 to 8 carbon atoms, 1, 2 or 3 alkoxy moieties of 1 to 6 carbon atoms, 1, 2 or 3 alkenoxy moieties of 2 to 6 carbon atoms; 1, 2 or 3 halogen atoms; 1 or 2 trifluoromethyl moieties; 1 or (b) 1 substituent selected from the group consisting of trifluoromethoxy, nitro, cyano, a moiety of the formula

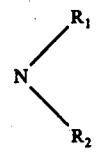

a carbonamido moiety of the formula

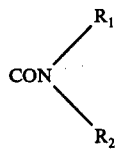

a sulphonamido moiety of the formula

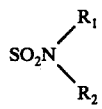

wherein $R_1$ and $R_2$ are each hydrogen or straight or branched chain alkyl of 1 to 4 carbon atoms, or $R_1$ and $R_2$ together with the nitrogen atom to which they are attached are linked together to form a 5-, 6- or 7-membered heterocyclic ring wherein the nitrogen atom is the only heteroatom or wherein oxygen is also present as a ring member, and $SO_n$-alkyl of 1 to 4 carbon atoms wherein n is zero, 1 or 2; or (c) an annellated branched or unbranched, saturated or unsaturated, 5-, 6- or 7-membered isocyclic or heterocyclic ring wherein said ring has up to 3 heteroatoms selected from the group consisting of 1 sulphur atom and 1 or 2 oxygen atoms, and wherein said naphthyl ring is unsubstituted and said phenyl ring is either unsubstituted or chloro-substituted.

According to another embodiment, R is anthryl or phenanthryl; or naphthyl unsubstituted or substituted by methyl, chloro, dichloro or trifluoromethyl; or phenyl substituted by (a) 1 or 2 identical or different substituents selected from the group consisting of chloro, bromo, fluoro and iodo;

(b) 3 of the same substituents selected from the group consisting of chloro, bromo and fluoro;

(c) 2 different substituents selected from the group consisting of chloro or bromo, lower alkyl, lower alkoxy, trifluoromethyl, trifluoromethoxy, nitro and cyano;

(d) 1, 2 or 3 lower alkyl moieties;

(e) 1 or 2 lower alkoxy moieties;

(f) phenyl, trifluoromethyl, trifluoromethoxy, nitro, cyano, $CONH_2$,

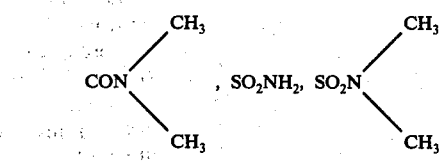

$SO_2CH_3$ or lower alkylmercapto;

(g) 2 different substituents selected from the group consisting of phenyl, chloro or bromo, alkyl of 1 to 4 carbon atoms, alkoxy of 1 to 4 carbon atoms, trifluoromethoxy, nitro, dimethylamino, $SO_2CH_3$ and $SO_2NH_2$; or (h) an annellated trimethylene, tetramethylene or methylenedioxy moiety and wherein the phenyl ring is unsubstituted or chloro-substituted.

According to another embodiment, R is naphthyl; or phenyl substituted by (a) 1 or 2 identical or different substituents selected from the group consisting of chloro, bromo, fluoro and iodo;

(b) 3 of the same substituents selected from the group consisting of chloro, bromo and fluoro;

(c) 2 different substituents selected from the group consisting of chloro or bromo, lower alkyl and lower alkoxy;

(d) 1 or 2 lower alkyl or lower alkoxy moieties;

(e) nitro, cyano, trifluoromethyl, trifluoromethoxy, or phenyl; or (f) an annellated trimethylene, tetramethylene or methylenedioxy moiety and wherein said phenyl ring is unsubstituted or chloro-substituted.

The method of effecting diuretic therapy, saluretic therapy, or anti-hypertensive therapy in humans and animals according to the present invention comprises administering to such human or animal a diuretically effective amount, a saluretically effective amount or an anti-hypertensive amount of a compound of the formula

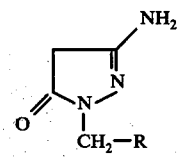

or a pharmaceutically acceptable non-toxic salt therof, wherein R is aryl which is either unsubstituted or substituted by (a) 1, 2 or 3 identical or different substituents selected from the group consisting of halogen, alkyl of 1 to 8 carbon atoms, alkoxy of 1 to 8 carbon atoms, alkenoxy of 2 to 6 carbon atoms, cycloalkyl of 5 to 7 carbon atoms, trifluoromethyl, trifluoromethoxy and phenyl;

(b) 1 or 2 identical or different substituents selected from the group consisting of nitro, cyano, lower alkylamino of 1 to 4 carbon atoms, a carbonamido moiety of the formula

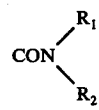

and a sulphonamido moiety of the formula

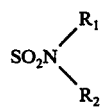

wherein $R_1$ and $R_2$ are each hydrogen or straight or branched chain alkyl of 1 to 4 carbon atoms, or $R_1$ and $R_2$ together with the nitrogen atom to which they are attached are linked together to form a 5-, 6- or 7-membered heterocycle ring wherein the nitrogen atom is the only heteroatom or wherein oxygen is also present as a ring member;

(c) 1 substituent selected from the group consisting of dialkylamino of 1 to 4 carbon atoms in each alkyl moiety, nitro, cyano and $SO_n$-alkyl of 1 to 4 carbon atoms wherein n is zero, 1 or 2;

(d) 1 substituent selected from the group consisting of a moiety of the formula

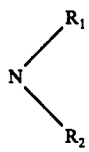

wherein $R_1$ and $R_2$ are as above defined, nitro, cyano, a carbonamido moiety of the formula

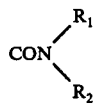

wherein $R_1$ and $R_2$ are as above defined, a sulphonamido moiety of the formula

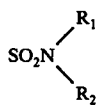

wherein $R_1$ and $R_2$ are as above defined and $SO_n$- alkyl of 1 to 4 carbon atoms wherein n is zero, 1 or 2, and 1 or 2 substituents selected from the group consisting of alkyl of 1 to 8 carbon atoms, alkoxy of 1 to 6 carbon atoms, halogen and trifluoromethyl;
  (e) an annellated branched or unbranched, saturated or unsaturated, 5-, 6- or 7-membered isocyclic or heterocyclic ring having 1 or more heteroatoms selected from the group consisting of oxygen and sulphur and wherein said aryl moiety is either unsubstituted or chlorosubstituted;
  (f) - O - $(CH_2)_{n'}$- $N(alkyl)_2$ wherein the alkyl groups contain a total of 2 to 4 carbon atoms and $n'$ is 2 or 3; or
  (g) 2 different substituents selected from the group consisting of alkyl of 1 to 8 carbon atoms, phenyl, halogen, alkoxy of 1 to 8 carbon atoms, trifluoromethyl, trifluoromethoxy, lower alkylamino, nitro, cyano, $SO_n$- alkyl of 1 to 4 carbon atoms wherein $n$ is zero, 1 or 2, a carbonamido moiety of the formula

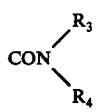

and a sulphonamido moiety of the formula

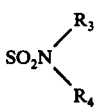

wherein $R_3$ and $R_4$ are each hydrogen or alkyl of 1 to 4 carbon atoms. According to one embodiment, R is aryl which is either unsubstituted or substituted by
  (a) 1, 2 or 3 identical or different substituents selected from the group consisting of halogen, trifluoromethyl, trifluoromethoxy, alkyl of 1 to 8 carbon atoms, alkoxy of 1 to 6 carbon atoms, alkenoxy of 2 to 6 carbon atoms, cycloalkyl of 5 to 7 carbon atoms and phenyl;
  (b) 1 substituent selected from the group consisting of a moiety of the formula

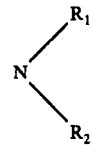

wherein $R_1$ and $R_2$ are each hydrogen or straight or branched chain alkyl of 1 to 4 carbon atoms, or $R_1$ and $R_2$ together with the nitrogen atom to which they are attached are linked together to form a 5-, 6- or 7-membered heterocyclic ring wherein the nitrogen atom is the only heteroatom or wherein oxygen is also present as a ring member, trifluoromethoxy, nitro, cyano, a carbonamido moiety of the formula

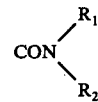

wherein $R_1$ and $R_2$ are as above defined, a sulphonamido moiety of the formula

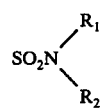

wherein $R_1$ and $R_2$ are as above defined and $SO_n$- alkyl of 1 to 4 carbon atoms wherein n is zero, 1 or 2, or by 1 of said substituents and 1 or 2 substituents selected from the group consisting of alkyl of 1 to 8 carbon atoms, alkoxy of 1 to 6 carbon atoms, halogen and trifluoromethyl; or
  (c) an annellated branched or unbranched, saturated or unsaturated, 5-, 6- or 7-membered isocyclic or heterocyclic ring having up to 4 heteroatoms selected from the group consisting of 1 to 2 oxygen atoms and 1 or 2 sulphur atoms, and wherein said aryl moiety is either unsubstituted or chloro-substituted.

According to another embodiment, R is anthryl or phenanthryl; or phenyl or naphthyl substituted by
  (a) a member selected from the group consisting of 1, 2 or 3 alkyl moieties of 1 to 8 carbon atoms, 1, 2 or 3 alkoxy moieties of 1 to 6 carbon atoms, 1, 2 or 3 alkenoxy moieties of 2 to 6 carbon atoms; 1, 2 or 3 halogen atoms; 1 or 2 trifluoromethyl moieties; 1 or 2 cycloalkyl moieties of 5 to 7 carbon atoms and phenyl;
  (b) 1 substituent selected from the group consisting of trifluoromethoxy, nitro, cyano, a moiety of the formula

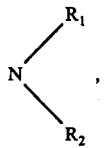

a carbonamido moiety of the formula

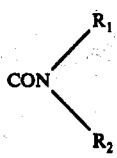

a sulphonamido moiety of the formula

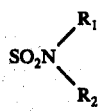

wherein $R_1$ and $R_2$ are each hydrogen or straight or branched chain alkyl of 1 to 4 carbon atoms, or $R_1$ and $R_2$ together with the nitrogen atom to which they are attached are linked together to form a 5-, 6- or 7-membered heterocyclic ring wherein the nitrogen atom is the only heteroatom or wherein oxygen is also present as a ring member, and $SO_n$- alkyl of 1 to 4 carbon atoms wherein n is zero, 1 or 2; or (c) an annellated branched or unbranched, saturated or unsaturated, 5-, 6- or 7-membered isocylic or heterocyclic ring wherein said ring has up to 3 heteroatoms selected from the group consisting of 1 sulphur atom and 1 or 2 oxygen atoms, and wherein said naphthyl ring is unsubstituted and said phenyl ring is either unsubstituted or chloro-substituted.

According to another embodiment, R is anthryl or phenanthryl; or naphthyl unsubstituted or substituted by methyl, chloro, dichloro or trifluoromethyl; or phenyl substituted by (a) 1 or 2 identical or different substituents selected from the group consisting of chloro, bromo, fluoro and iodo;
(b) 3 of the same substituents selected from the group consisting of chloro, bromo and fluoro;
(c) 2 different substituents selected from the group consisting of chloro or bromo, lower alkyl, lower alkoxy, trifluoromethyl, trifluoromethoxy, nitro and cyano;
(d) 1, 2 or 3 lower alkyl moieties;
(e) 1 or 2 lower alkoxy moieties;
(f) phenyl, trifluoromethyl, trifluoromethoxy, nitro, cyano, $CONH_2$,

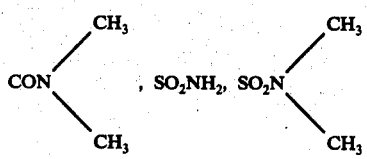

$SO_2CH_3$ or lower alkylmercapto;

(g) 2 different substituents selected from the group consisting of phenyl, chloro or bromo, alkyl of 1 to 4 carbon atoms, alkoxy of 1 to 4 carbon atoms, trifluoromethoxy, nitro, dimethylamino, $SO_2 CH_3$ and $SO_2NH_2$; or
(h) an annellated trimethylene, tetramethylene or methylenedioxy moiety and wherein the phenyl ring is unsubstituted or chloro-substituted.

According to another embodiment, R is naphthyl; or phenyl substituted by (a) 1 or 2 identical or different substituents selected from the group consisting of chloro, bromo, fluoro and iodo;
(b) 3 of the same substituents selected from the group consisting of chloro, bromo and fluoro;
(c) 2 different substituents selected from the group consisting of chloro or bromo, lower alkyl and lower alkoxy;
(d) 1 or 2 lower alkyl or lower alkoxy moieties;
(e) nitro, cyano, trifluoromethyl, trifluoromethoxy, or phenyl; or
(f) an annellated trimethylene, tetramethylene or methylenedioxy moiety and wherein said phenyl ring is unsubstituted or chloro-substituted.

The pharmaceutical compositions of the present invention contain a major or minor amount, e.g. from 99.5 to 0.1%, preferably 90% to 0.5%, of at least one 1-aryl-3-amino-pyrazol-5-one as herein defined in combination with a pharmaceutical carrier, the carrier comprising one or more solid, semi-solid or liquid diluent, fi,ler and formulation adjuvant which is non-toxic, inert and pharmaceutically acceptable. Such pharmaceutical compositions are preferably in dosage unit form; i.e. physically discrete units containing a predetermined amount of the drug corresponding to a fraction or multiple of the dose which is calculated to produce the desired therapeutic response. The dosage units can contain one, two, three, four or more single doses or, alternatively, one-half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgment and considering the age, weight and condition of the recipient, the route of administration and the nature and gravity of the illness, generally the dosage for parenteral administration will be from 0.5mg to 4.5g, preferably 5 to 900mg. The preferred oral administration is 5mg to 45g, preferably 25mg to 9g. In each case, the dosage represents the amount of active ingredients to be administered. The daily dosage on parenteral administration is preferably 0.01 to 50mg/kg, particularly 0.1 to 10mg/kg, and for oral administration is 0.1 to 500mg/kg, particularly 0.5 to 100mg/kg. In some instances a sufficient therapeutic effect can be obtained at a lower dose while in others, a larger dose will be required.

Oral administration can be effected utilizing solid and liquid dosage unit forms such as powders, tablets, dragees, capsules, granulates, suspensions, solutions and the like.

Powders are prepared by comminuting the compound to a suitable fine size and mixing with a similarly comminuted pharmaceutical carrier such as an edible carbohydrate as for example starch, lactose, sucrose, glucose or mannitol. Sweetening, flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated for example by preparing a powder mixture, granulating or slugging, adding a lubricant and disintegrant and pressing into tablets. A powder mixture is prepared by mixing the compound, suitably comminuted, with a diluent or base as described above, and optionally with a binder such as carboxymethyl cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous sucrose solution while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a non-toxic liquid vehicle suitable for injection such as an aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Non-toxic salts and salt solutions can be added to render the injection isotonic. Stabilizers, preservatives and emulsifiers can also be added.

Rectal administration can be effected utilizing suppositories in which the compound is admixed with low melting water soluble or insoluble solids such as polyethylene glycol, cocoa butter, higher esters as for example myristyl palmitate, or mixtures thereof. Oral and parenteral administration are preferred.

The water soluble salts of the 1-substituted-3-aminopyrazol-5-ones are particularly useful such as the sodium, potassium ethanolamine, diethanolamine, triethanolamine, amino-trihydroxymethyl-methane, glucosamine and N-methylglucosamine salts.

To demonstrate the diuretic and saluretic effect of the compounds according to the invention, 3-amino-1-(4-chloro-3-bromobenzyl)-pyrazol-5-one described in Example 12 was administered to dogs and rats.

1. Experiment on dogs:

(a) Method:

Beagle bitches received on the day of the experiment, every 30 minutes, 1 ml/kg body weight of a solution which contained 0.4% of NaCl and 0.2% of KCl and was given by means of a probang. The urine formed during the first 60 minutes was discarded. Thereafter, the test preparation was administered orally as 0.5 mg/kg of an 0.1% strength tragacanth mucin, and the urine was collected for 3 hours. The renal excretion in $\mu$ equivalent/kg/3 hours was calculated from the volume of urine (ml/kg) and the measured electrolyte concentration (mmol/l). Sodium and potassium were determined by flame photometry and chloride was determined potentiometrically.

(b) Results:

The results are shown in Table 1. The renal excretion of sodium and water is substantially increased after oral administration of the test preparation. The effect depends on the dose. Even after only 1 mg/kg administered orally, the excretion of sodium is increased fivefold relative to the treated control animals. On the other hand, the excretion of potassium is only doubled after this dose.

Table I

|  | Excretion in ml or $\mu$ equivalent/kg/3 hours | | | |
| --- | --- | --- | --- | --- |
|  | Water | Sodium | Chloride | Potassium |
| Control | 7.7 ± 1.8 | 471 ± 335 | 787 ± 283 | 374 ± 100 |
| 0.3 mg/kg p.o. | 7.9 | 644 | 966 | 292 |
| 1 mg/kg p.o. | 20.2 | 2,539 | 3,054 | 600 |
| 3 mg/kg p.o. | 40.1 | 4,577 | 5,746 | 1,110 |

Electrolyte excretion and water excretion in dogs under the action of 3-amino-1-(4-chloro-3-bromobenzyl)-pyrazol-5-one. Average values of 2 animals at a time (control = 5 animals).
"p.o." = per os.

2. Experiment on rats:

(a) Methods:

Male SPF rats of the Wistar strain received 10 Ml/kg of 0.1% strength tragacanth mucin by means of a probang. The test preparation, in mg/kg, was administered with this liquid. The animals were then placed in pairs in diuresis cages. The urine collection period lasted 5 hours. The collected urine was filtered and analysed chemically.

(b) Results:

The results of the experiments are shown in Table II. In rats, also, oral administration of the test preparation is followed by a dosage-dependent increase in the excretion of NaCl and of water. As in the case of dogs, the excretion of sodium is substantially more strongly influenced than the excretion of potassium.

Table II

|  | Excretion in ml or $\mu$ equivalent/kg/5 hours | | | |
| --- | --- | --- | --- | --- |
|  | Water | Sodium | Chloride | Potassium |
| Control | 19.8±1.8 | 445± 81 | 797±112 | 561± 72 |
| 3 mg/kg p.o. | 32.1±4.4 | 2,010±534 | 2,700±601 | 795±103 |
| 10 mg/kg p.o. | 48.8±3.8 | 3,819±385 | 4,910±440 | 1,134± 88 |

Table II-continued

| | Excretion in ml or μ equivalent/kg/5 hours | | | |
|---|---|---|---|---|
| | Water | Sodium | Chloride | Potassium |
| 30 mg/kg p.o. | 67.2±2.7 | 5,916±199 | 7,482±288 | 1,572± 61 |

Excretion of electrolyte and excretion of water in rats under the influence of 3-amino-1-(4-chloro-3-bromobenzyl)-pyrazol-5-one. Average values and scatter s of 16 animals at a time.
"p.o." = per os.

Using the method described in the preceding experiment on rats, the effect of the compounds of Examples 7 and 1 on rats were also tested. The results of this test are shown in Tables III and IV which follow.

Table III

| | Excretion in ml or μ equivalent/kg/5 hours | | | |
|---|---|---|---|---|
| | Water | Sodium | Chloride | Potassium |
| Control | 20.5±0.8 | 817± 81 | 1,011± 72 | 364±35 |
| 30 mg/kg p.o. | 15.3±1.2 | 627± 72 | 917± 87 | 335±51 |
| 100 mg/kg p.o. | 22.6±2.9 | 1,281±289 | 2,095±358 | 710±75 |

Excretion of electrolyte and excretion of water in rats under the influence of the compound of Example 7. Average values and scatter for 10 animals at a time.
"p.o." = per os.

Table IV

| | Excretion in ml or μ equivalent/kg/5 hours | | | |
|---|---|---|---|---|
| | Water | Sodium | Chloride | Potassium |
| Control | 20.5±0.8 | 817± 81 | 1,011± 72 | 364±35 |
| 30 mg/kg p.o. | 21.7±1.1 | 1,254± 92 | 1,911± 91 | 453±28 |
| 100 mg/kg p.o. | 49.8±0.8 | 4,394±218 | 5,837±162 | 1,304±51 |

Excretion of electrolyte and excretion of water in rats under the influence of the compound of Example 1. Average values and scatter for 10 animals at a time.
"p.o." = per os.

3. Experiment on dogs:

(a) Method:

Beagle bitches received on the day of the experiment, every 30 minutes, 1 ml/kg body weight of a solution which contained 0.4% of NaCl and 0.2% of KCl and was given by means of a probang. The urine formed during the first 60 minutes was discarded. Thereafter, the test preparation, containing as the active agent the compound of Example 45, was administered orally as 0.5 mg/kg of an 0.1% strength tragacanth mucin, and the urine was collected for 2 hours. The renal excretion in μ equivalent/kg/2 hours was calculated from the volume of urine (ml/kg) and the measured electrolyte concentration (mmol/l). Sodium and potassium were determined by flame photometry and chloride was determined potentiometrically.

(b) Results:

The results are shown in Table V. The renal excretion of sodium and water is substantially increased after oral administration of the test preparation. The effect depends on the dose. After 10 mg/kg administered orally, the excretion of sodium is increase ten-fold relative to the treated control animals. On the other hand, the excretion of potassium is only doubled after this dose.

Table V

| | Excretion in ml or μ equivalent/kg/2 hours | | | |
|---|---|---|---|---|
| | Water | Sodium | Chloride | Potassium |
| Control | 5.2±0.5 | 240±74 | 501±64 | 250±72 |
| 3 mg/kg p.o. | 8.5±0.8 | 773±0.3 | 1,087±119 | 289±51 |
| 10 mg/kg p.o. | 18.5±2.5 | 2,370±499 | 2,826±567 | 471±54 |

Table V-continued

| | Excretion in ml or μ equivalent/kg/2 hours | | | |
|---|---|---|---|---|
| | Water | Sodium | Chloride | Potassium |
| 30 mg/kg p.o. | 30.1±3.0 | 3,531±478 | 4,070±593 | 848±273 |

Effect of 3-amino-1-(4-chlorobenzyl)-pyrazol-5-one (administered perorally) on the renal excretion of electrolyte and water of awake dogs. Mean values and scatter from groups of 4 animals.

4. Experiment on rats:

(a) Methods:

Male SPF rats of the Wistar strain received 10 ml/kg of 0.1% strength tragacanth mucin by means of a probang. The test preparation containing as the active agent the compound of Example 45, in mg/kg was administered with this liquid. The animals were then placed in pairs in diuresis cages. The urine collection period lasted 5 hours. The collected urine was filtered and analysed chemically.

(b) Results:

The results of the experiments are shown in Table VI. In rats, also, oral administration of the test preparation is followed by a dosage-dependent increase in the excretion of NaCl and of water. As in the case of dogs, the excretion of sodium is substantially more strongly influenced than the excretion of potassium.

Table VI

| | Excretion in ml or μ equivalent/kg/5 hours | | | |
|---|---|---|---|---|
| | Water | Sodium | Chloride | Potassium |
| Control | 20±1.6 | 470±89 | 947±136 | 597±54 |
| 10 mg/kg p.o. | 28.0±2.5 | 694±125 | 1,232±104 | 771±64 |
| 30 mg/kg p.o. | 31.9±1.9 | 1,471±101 | 2,249±129 | 763±75 |
| 100 mg/kg p.o. | 66.4±2.8 | 4,973±275 | 6,956±253 | 1,246±94 |

Effect of peroral administration of 3-amino-1-(4-chlorobenzyl)-pyrazol-5-on on excretion of electrolyte and water by rats. Mean values and scatter of groups of 16 animals.

5. Experiment on Rats:

The effects of the compositions having as active agent the compound of Examples 2 and 7 were also tested on rats, using the method described in the preceding Experiment on Rats (4). The results of this test are shown in Tables VII and VIII which follow.

Table VII

| | Excretion in ml or μ equivalent/kg/5 hours | | | |
|---|---|---|---|---|
| | Water | Sodium | Chloride | Potassium |
| Control | 20.5±0.8 | 817±81 | 1,011±72 | 364±35 |
| 30 mg/kg p.o. | 15.3±1.2 | 627±72 | 917±87 | 335±51 |
| 100 mg/kg p.o. | 22.6±2.9 | 1,281±289 | 2,095±358 | 710±75 |

Excretion of electrolyte and of water by rats after peroral administration of the compound of Example 12. Mean values and scatter of groups of 10 animals.

Table VIII

| | Excretion in ml or μ equivalent/kg/5 hours | | | |
|---|---|---|---|---|
| | Water | Sodium | Chloride | Potassium |
| Control | 20.5±0.8 | 817±81 | 1,011±72 | 364±35 |
| 30 mg/kg p.o. | 21.7±1.1 | 1,254±92 | 1,911±91 | 453±28 |
| 100 mg/kg p.o. | 49.8±0.8 | 4,394±218 | 5,837±162 | 1,304±51 |

Excretion of electrolyte and of water by rats after peroral administration of the compound of Example 7. Mean values and scatter of groups of 10 animals.

The following non-limitative examples more particularly illustrate the present invention.

EXAMPLE 1

3-Amino-1-(4-bromobenzyl)-pyrazol-5-one

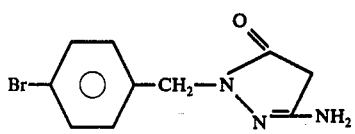

9.2 g of metallic sodium are dissolved in 200 ml of ethanol. A mixture of 25 g of cyanoacetic acid ethyl ester and 35 g of p-bromobenzylhydrazine in 50 ml of ethanol is then added at room temperature. The mixture is warmed to 60° C for 2 hours, the substance which was precipitated is filtered off and the filtrate is evaporated. The residue is taken up with water, the mixture is shaken with ether and the aqueous phase is acidified with dilute acetic acid. The crude product is purified by twice recrystallising it from alcohol.

17 g of the compound identified above as felted needles of melting point 139°, corresponding to 36% of theory, are obtained.

EXAMPLE 2

3-Amino-1-(4-bromobenzyl)-pyrazol-5-one

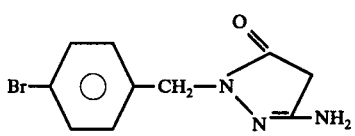

17.5 g of β-amino-β-ethoxyacrylic acid ethyl ester and 20 g of 4-bromobenzylhydrazine, on stirring for 5 hours in alcohol at 50° and working up as described in Example 1, yield 15.6 g of the compound identified above, corresponding to 58% of theory, as colorless crystals of melting point 139°.

EXAMPLE 3

3-Amino-1-(4-fluorobenzyl)-pyrazol-5-one

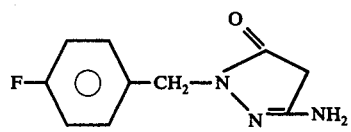

17.5 g of β-amino-β-ethoxyacrylic acid ethyl ester and 13 g of 4-fluorobenzylhydrazine, on stirring for 5 hours in ethanol at 60° and working up as described in Example 1, yield 13.2 g of the compound identified above as colorless crystals of melting point 148°, corresponding to 63% of theory.

EXAMPLE 4

3-Amino-1-(3-fluorobenzyl)-pyrazol-5-one

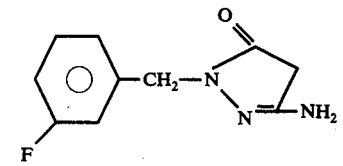

17.5 g of β-amino-β-ethoxyacrylic acid ethyl ester and 13 g of 3-fluorobenzylhydrazine, on stirring for 5 hours in ethanol at 60° and working up as described in Example 1, yield 11.3 g, corresponding to 55% of theory, of the compound identified above as colorless crystals of melting point 129°.

EXAMPLE 5

3-Amino-1-(4-methylbenzyl)-pyrazol-5-one

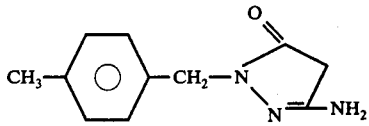

17.5 g of β-amino-β-ethoxyacrylic acid ethyl ester and 13.6 g of 4-methylbenzylhydrazine are introduced into 75 ml of pyridine. The mixture is stirred for 8 hours at room temperature and the pyridine is driven off under reduced pressure. The residue is treated with a solution of 4.6 g of Na in 100 ml of ethanol and the mixture is warmed to 60° for 1 hour. The alcohol is driven off and the residue is taken up in 100 ml of water. The aqueous phase is extracted with ether, clarified with charcoal and acidified. A yellow-colored precipitate is obtained, which melts at 149° after recrystallisation from alcohol. The yield is 7.3 g of the compound identified above, corresponding to 36% of theory.

EXAMPLE 6

3-Amino-1-(3-methylbenzyl)-pyrazol-5-one

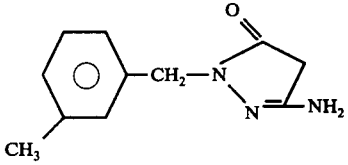

4.6 g of sodium are dissolved in 100 ml of ethanol. A mixture of 12 g of cyanoacetic acid ethyl ester and 13.6 g of 3-methylbenzylhydrazine is added to this solution. The mixture is heated to the boil for 5 hours while stirring and passing $N_2$ into it. After driving off the solvent, taking up the residue in water, extracting with ether and clarifying with animal charcoal, acidification with acetic acid yields colorless crystals which after again being recrystallised from ethanol melt at 92°. The yield is 10.3 g of the compound identified above, corresponding to 51% of theory.

EXAMPLE 7

3-Amino-1-(3,4-dimethylbenzyl)-pyrazol-5-one

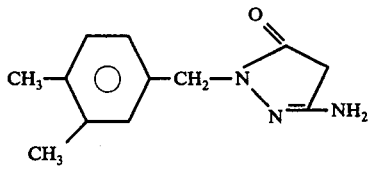

17.5 g of β-amino-β-ethoxyacrylic acid ethyl ester and 15 g of 3,4-dimethylbenzylhydrazine yield, analogously to the procedure described in Example 1, 16 g of the compound identified above as colorless small needles of melting point 160°, corresponding to 74% of theory.

EXAMPLE 8

3-Amino-1-(1,4-dimethyl)-pyrazol-5-one

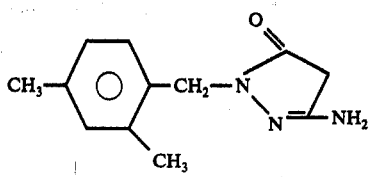

17.5 g of β-amino-β-ethoxyacrylic acid ethyl ester and 15 g of 2,4-dimethylbenzylhydrazine, analogously to the procedure described in Example 1, yield 14.3 g of the compound identified above, corresponding to 66% of theory, of melting point 151°.

EXAMPLE 9

3-Amino-1-(4-nitrobenzyl)-pyrazol-5-one

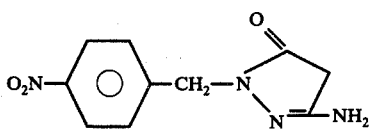

17.5 g of β-amino-β-ethoxyacrylic acid ethyl ester and 16.7 g of 4-nitrobenzylhydrazine, analogously to the procedure described in Example 1 yield 17.3 g of the compound identified above as yellowish crystals of melting point 182°, corresponding to 74% of theory.

EXAMPLE 10

3-Amino-1-(3-nitrobenzyl)-pyrazol-5-one

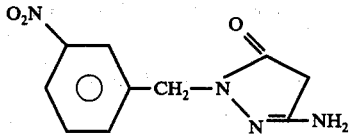

17.5 g of β-amino-β-ethoxyacrylic acid ethyl ester and 16.7 g of 3-nitrobenzylhydrazine, analogously to the procedure described in Example 1 yield 12.3 of the compound identified above as yellow crystals of melting point 163°, corresponding to 52% of theory.

EXAMPLE 11

3-Amino-1-(1-bromobenzyl)-pyrazol-5-one

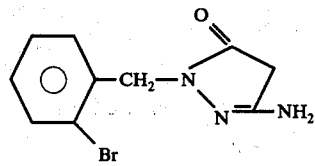

42.4 g of 2-bromobenzylhydrazine were added dropwise, under nitrogen, to a solution of 33.4 g of β-amino-βethoxyacrylic acid methyl ester and 1 g of p-toluenesulphonic acid in 250 ml of ethanol. After stirring for 15 hours at room temperature, the solution was concentrated in vacuo and the precipitate which had formed was filtered off and dissolved in 2 N sodium hydroxide solution. The alkaline solution was again extracted with ether and subsequently slightly acidified with dilute acetic acid, whereupon the compound identified above precipitated. After recrystallisation from methanol, this product melted at 168°–169°. 27.5 g (49%).

EXAMPLE 12

3-Amino-1-(3-bromo-4-chlorobenzyl)-pyrazol-5-one

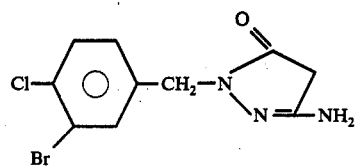

49 g of β-amino-β-ethoxyacrylic acid ethyl ester and 2 g of p-toluenesulphonic acid were dissolved in 225 ml of ethanol and 72 g of 3-bromo-4-chlorobenzylhydrazine were added under nitrogen. After standing overnight, the compound identified above had settled out as a precipitate and was filtered off and recrystallised twice from ethanol. Melting point: 171°–172° C, 40 g (43%).

EXAMPLE 13

3-Amino-1-(3-chloro-4-bromobenzyl)-pyrazol-5-one

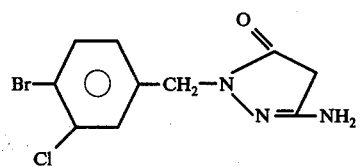

48.8 g of 4-bromo-3-chlorobenzylhydrazine are added dropwise under nitrogen to a solution of 33.2 g of β-amino-β-ethoxyacrylic acid ethyl ester and 1.5 g of toluenesulphonic acid in 150 ml of ethanol. After stirring for a further two hours, the mixture was left to stand and the compound identified above began to crystallise out after four hours. It was filtered off and twice recrystallised from ethanol. Melting point: 145°–146°, 23 g (37%).

EXAMPLE 14

3-Amino-1-(2,4,5-trichlorobenzyl)-pyrazol-5-one

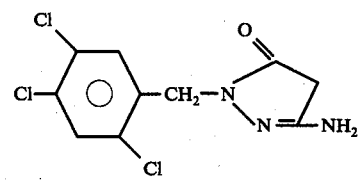

54.7 g of β-amino-β-ethoxyacrylic acid ethyl ester and 2 g of p-toluenesulphonic acid were dissolved in 400 ml of ethanol. A solution of 77.6 g of 2,4,5-trichlorobenzylhydrazine in 200 ml of ethanol was added dropwise thereto, under nitrogen. After stirring for a further two hours, the mixture was left to stand overnight and the precipitate which had separated out was filtered off and dissolved in 2 N sodium hydroxide solution. The alkaline solution was repeatedly extracted with ether and subsequently slightly acidified with dilute acetic acid, whereupon the compound identified above precipitated. After recrystallisation from ethanol, this product melted at 195°–196°. 38 g (38%).

EXAMPLE 15

3-Amino-1-(3-chloro-4-methylbenzyl)-pyrazol-5-one

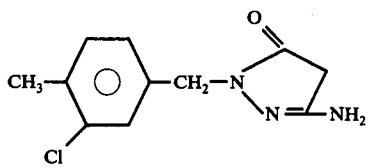

50 g of 4-methyl-3-chlorobenzylhydrazine were added dropwise, under nitrogen, to a solution of 46.7 g of β-amino-β-ethoxyacrylic acid ethyl ester and 1.5 g of p-toluenesulphonic acid in 200 ml of ethanol. After stirring for a further two hours, the compound identified above precipitated. It was filtered off and recrystallised from ethanol. Melting point: 130°–131°, 35 g (50%).

EXAMPLE 16

3-Amino-1-(4-phenylbenzyl)-pyrazol-5-one

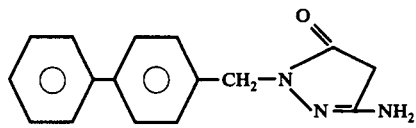

A solution of 29 g of 4-phenylbenzylhydrazine in 60 ml of ethanol was added dropwise, under nitrogen, to a solution of 23.4 g (0.147 mol) of β-amino-β-ethoxyacrylic acid ethyl ester and 1 g of p-toluenesulphonic acid in 100 ml of ethanol. During addition the temperature rose from 22° to 32° C. After standing overnight, the reaction solution was concentrated in vacuo, the precipitate which separated out was dissolved in 2 N sodium hydroxide solution and the alkaline solution was repeatedly extracted with ether. Addition of dilute acetic acid until the mixture reacted weakly acid yielded the compound identified above, which melted at 185°–186° after recrystallisation from ethanol. 13 g (33%).

EXAMPLE 17

3-Amino-1-(β-naphthylmethyl)-pyrazol-5-one

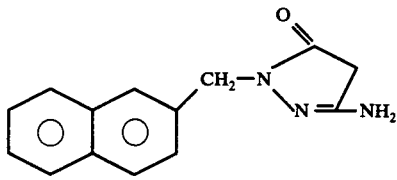

A solution of 40.5 g of N-(β-hydrazino-methylnaphthalene) was added dropwise, under nitrogen, to a solution of 37.5 g of β-amino-β-ethoxyacrylic acid ethyl ester and 1 go of p-toluenesulphonic acid in 100 ml of ethanol. The mixture was stirred for 2 hours longer. After a further 2 hours, the product identified above precipitated and was filtered off and recrystallised from ethanol. Melting point: 156°–157°, 22 g (39%).

EXAMPLE 18

3-Amino-1-(2,5-dimethylbenzyl)-pyrazol-5-one

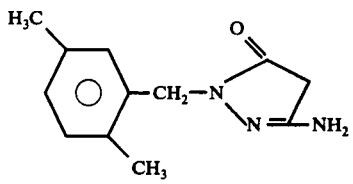

26.6 g of 2,5-dimethylbenzylhydrazine were added dropwise to a solution of 28.2 g of β-amino-β-ethoxyacrylic acid ethyl ester and 1 g of p-toluenesulphonic acid in 130 ml of ethanol, in the course of which the temperature rose from 25° to 35° C. After stirring overnight, the compound identified above separated out, and was filtered off and recrystallised from ethanol. Melting point: 124°, 20 g (52%).

EXAMPLE 19

3-Amino-1-(4-trifluoromethoxybenzyl)-pyrazol-5-one

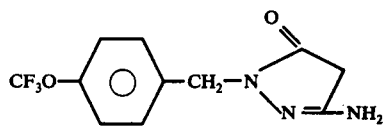

From 17.5 g of β-amino-β-ethoxyacrylic acid ethyl ester and 20.6 g of 4-trifluoromethoxybenzylhydrazine, analogously to the procedure described in Example 1. 8.7 g of the compound identified above as colorless crystals of melting point 99°, corresponding to 32% of theory, are obtained.

EXAMPLE 20

3-Amino-1-(3,4-methylenedioxybenzyl)-pyrazol-5-one

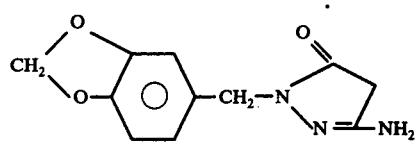

From 17.5 g of β-amino-β-ethoxyacrylic acid ethyl ester and 16.6 g of 3,4-methylenedioxybenzylhydrazine, analogously to the procedure described in Example 1. 12.1 g of the compound identified above, as colorless crystals of melting point 218°, corresponding to 52% of theory, are obtained.

EXAMPLE 21

3-Amino-1-(3,4-tetramethylenebenzyl)-pyrazol-5-one

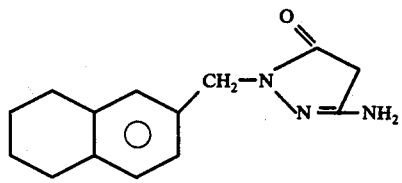

From 17.5 g of β-amino-β-ethoxyacrylic acid ethyl ester and 17.6 g of 3,4-tetramethylenebenzylhydrazine, analogously to the procedure described in Example 1. After recrystallisation from alcohol, 15.6 g of the compound identified above, as colorless crystals of melting point 103°, are obtained. The compound crystallises with one mol of alcohol of recrystallisation. The yield is 54% of theory.

EXAMPLE 22

3-Amino-1-(2-methylbenzyl)-pyrazol-5-one

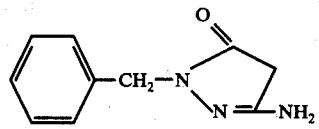

27.5 g of o-methylbenzylhydrazine, dissolved in 100 ml of ethanol, were added dropwise at room temperature to a solution of 32 g of β-amino-β-ethoxyacrylic acid ethyl ester and 1.5 g of p-toluenesulphonic acid in 300 ml of ethanol. After standing overnight, the reaction solution was concentrated in vacuo and the compound identified above, which separated out as a precipitate, was filtered off and recrystallised from ethanol. Melting point: 138°, 15 g (37%).

EXAMPLE 23

3-Amino-1-(3-bromobenzyl)-pyrazol-5-one

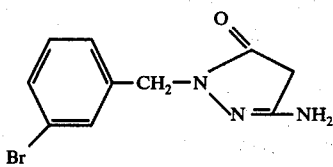

20.5 g of β-amino-β-ethoxyacrylic acid ethyl ester together with 1.5 g of p-toluenesulphonic acid were dissolved in 200 ml of ethanol. 26 g of m-bromobenzylhydrazine were added dropwise to this solution, under nitrogen. After stirring for 2 hours, the mixture was left to stand overnight and the compound identified above, which had separated out as a precipitate, was filtered off and recrystallised from ethanol. Melting Point: 160°, 12 g (35%).

EXAMPLE 24

3-Amino-1-(3-iodobenzyl)-pyrazol-5-one

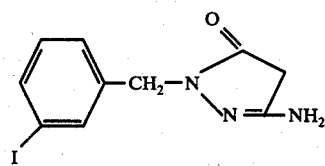

A solution of 45 g of m-iodobenzylhydrazine in 70 ml of ethanol was added dropwise to a solution of 28.6 g of β-amino-β-ethoxyacrylic acid ethyl ester and 1.5 g of p-toluenesulphonic acid in 350 ml of ethanol. After stirring overnight, the compound identified above had separated out as a precipitate and was filtered off and recrystallised from ethanol. Melting point: 186°, 16 g (28%).

EXAMPLE 25

3-Amino-1-(4-iodobenzyl)-pyrazol-5-one

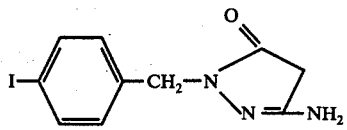

A solution of 25.5 g of p-iodobenzylhydrazine in 100 ml of ethanol was added dropwise, under nitrogen, to a solution of 16.2 g of β-amino-β-ethoxyacrylic acid ethyl ester and 1 g of p-toluenesulphonic acid in 250 ml of ethanol. After stirring overnight, the solvent was distilled off in vacuo and the compound identified above was obtained as a residue and recrystallised from ethanol. Melting point: 158°, 15 g (47%).

EXAMPLE 26

3-Amino-1-(2-fluorobenzyl)-pyrazol-5-one

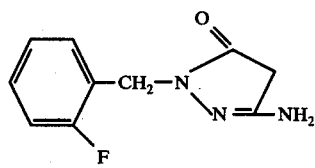

30.2 g of β-amino-β-ethoxyacrylic acid ethyl ester together with 2 g of p-toluenesulphonic acid were dissolved in 300 ml of ethanol and 27.1 g of o-fluorobenzylhydrazine were added under nitrogen. After stirring for two hours, the mixture was left to stand overnight and the compound identified above, which had separated out as a precipitate, was filtered off and recrystallised from ethanol. Melting point: 146°, 11 g (27%).

EXAMPLE 27

3-Amino-1-(3-chloro-6-fluorobenzyl)-pyrazol-5-one

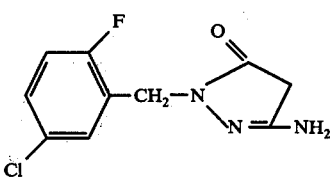

21.6 g of 2-fluoro-5-chlorobenzylhydrazine were added dropwise under nitrogen to a solution of 19.8 g of β-amino-β-ethoxyacrylic acid ethyl ester and 0.5 g of p-toluenesulphonic acid in 100 ml of ethanol, in the course of which the temperature rose from 20° to 30°. After stirring for two hours, the mixture was left to stand overnight and the compound identified above, which had separated out as a precipitate, was filtered off and recrystallised from ethanol. Melting point: 160°, 17 g (57%).

EXAMPLE 28

3-Amino-1-(3,4-dibromobenzyl)-pyrazol-5-one

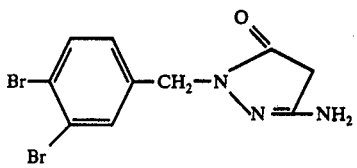

12.2 g of β-amino-β-ethoxyacrylic acid ethyl ester together with 1 g of p-toluenesulphonic acid were dissolved in 200 ml of ethanol. A solution of 21.6 g of 3,4-dibromobenzylhydrazine in 50 ml of ethanol was added dropwise thereto, under nitrogen. After stirring overnight, the solvent was concentrated in vacuo and the compound identified above, which had separated out as a precipitate, was filtered off and recrystallised from ethanol. Melting point: 182°, 11 g (41%).

EXAMPLE 29

3-Amino-1-(3-methyl-4-chlorobenzyl)-pyrazol-5-one

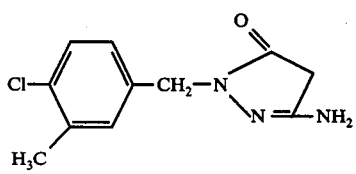

20.5 g of 3-methyl-4-chlorbenzylhydrazine were added dropwise, under nitrogen, to a solution of 19.1 g of β-amino-β-ethoxyacrylic acid ethyl ester and 1.5 g of p-toluenesulphonic acid in 200 ml of ethanol. The reaction solution was stirred overnight and the compound identified above, which had separated out as a precipitate, was filtered off and recrystallised from ethanol. Melting point: 131°, 10 g (35%).

EXAMPLE 30

3-Amino-1-(4-tert.butylbenzyl)-pyrazol-5-one

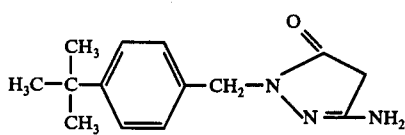

24.6 g of p-tert.butylbenzylhydrazine were added dropwise, under nitrogen, to a solution of 22 g of β-amino-β-ethoxyacrylic acid ethyl ester and 1 g of p-toluenesulphonic acid in 100 ml of ethanol, in the course of which the temperature rose from 24° to 30° C. After stirring overn the solvent was distilled off in vacuo and the oily residue solidified after addition of 50 ml of petroleum ether. The compound identified above was filtered off and recrystallised from ethanol. Melting point: 126°, 8 g (24%).

EXAMPLE 31

3-Amino-1-(4-isopropylbenzyl)-pyrazol-5-one

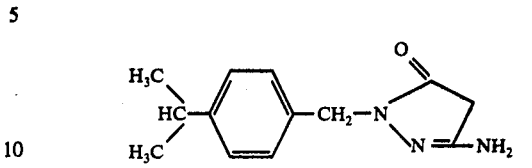

32 g of p-isopropylbenzylhydrazine were added, under nitrogen, to a solution of 31.8 g of β-amino-β-ethoxyacrylic acid ethyl ester and 1 g of p-toluenesulphonic acid in 150 ml of ethanol. After stirring for a further two hours, the mixture was left to stand overnight. The compound identified above, which separated out as a precipitate, was filtered off and recrystallised from ethanol. Melting point: 105°, 18.3 g (40%).

EXAMPLE 32

3-Amino-1-(3,4-trimethylenebenzyl)-pyrazol-5-one

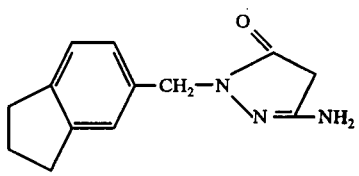

15.1 g of 5-hydrazinomethylindane-(3), dissolved in 50 ml of ethanol, were added dropwise, under nitrogen, to a solution of 14.8 g of β-amino-β-ethoxyacrylic acid ethyl ester and 1 g of p-toluenesulphonic acid in 100 ml of ethanol. After stirring overnight, the compound identified above had precipitated; it was filtered off and recrystallised from ethanol. Melting point: 146°, 9 g (42%).

EXAMPLE 33

3-Amino-1-(2-chloro-4-fluorobenzyl)-pyrazol-5-one

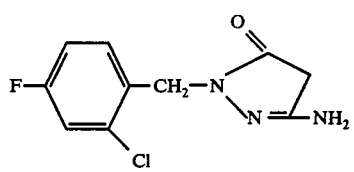

53.8 g of 2-chloro-4-fluorobenzylhydrazine were added dropwise, under nitrogen, to a solution of 49.2 g of β-aminoβ-ethoxyacrylic acid ethyl ester and 1 g of p-toluenesulphonic acid in 250 ml of ethanol, in the course of which the temperature rose from 22° to 32° C. After standing overnight, the compound identified above, which had separated out as a precipitate, was filtered off and recrystallised from ethanol. Melting point: 192°, 25 g (34%).

EXAMPLE 34

3-Amino-1-(3-n-butoxybenzyl)-pyrazol-5-one

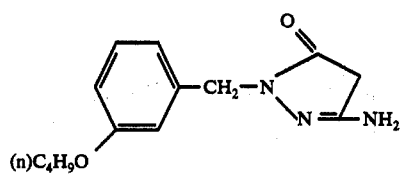

18 g of 3-n-butoxybenzylhydrazine were added dropwise, under nitrogen, to a solution of 14.8 g of β-amino-β-ethoxyacrylic acid ethyl ester and a pinch of p-toluenesulphonic acid in 180 ml of ethanol. After stirring for 2 hours, the mixture was left to stand overnight. The compound identified above, which had separated out as a precipitate, was filtered off and recrystallised from ethanol. Melting point: 110°, 8 g (33%).

EXAMPLE 35

3-Amino-1-(3-methoxy-4-chlorobenzyl)-pyrazol-5-one

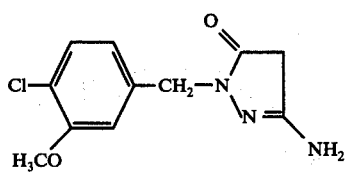

59 g of 4-chloro-3-methoxybenzylhydrazine were added dropwise, under nitrogen, to a solution of 50.5 g of β-aminoβ-ethoxyacrylic acid ethyl ester and 1.5 g of p-toluenesulphonic acid in 250 ml of ethanol. After standing overnight, the compound identified above, which had separated out as a precipitate, was filtered off and recrystallised from ethanol. Melting point: 148°, 30 g. (38%).

EXAMPLE 36

3-Amino-1-(2-nitrobenzyl)-pyrazol-5-one

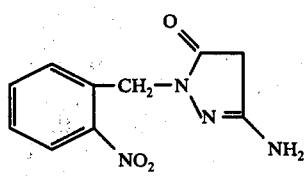

47.8 g of o-nitrobenzylhydrazine were added dropwise, under nitrogen, to a solution of 45.5 g of β-amino-β-ethoxyacrylic acid ethyl ester and a pinch of p-toluenesulphonic acid in 200 ml of ethanol. After standing overnight, the solvent was distilled off in vacuo and the residue was treated with a 2:1 mixture of ether and ethanol. The compound identified above which thereupon precipitated was filtered off and recrystallised from ethanol. Melting point: 190°, 23 g (34%).

EXAMPLE 37

3-Amino-1-(3-n-propoxy-4-chlorobenzyl)-pyrazol-5-one

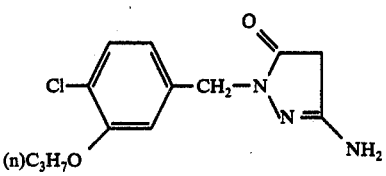

77 g of 4-chloro-3-(n)-propoxybenzylhydrazine were added, under nitrogen, to a solution of 55.6 g of β-amino-β-ethoxyacrylic acid ethyl ester and 1 g of p-toluenesulphonic acid in 300 ml of ethanol. After stirring overnight, the solvent was distilled off in vacuo and the product which thereupon precipitated was filtered off and recrystallised from ethanol. Melting point: 143°, 25 g (25%).

EXAMPLE 38

3-Amino-1-(3-ethoxy-4-chlorobenzyl)-pyrazol-5-one

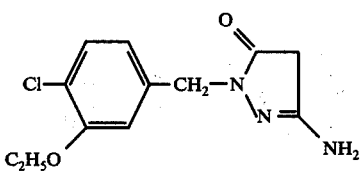

45.5 g of 4-chloro-3-ethoxybenzylhydrazine were added, under nitrogen, to a solution of 35 g of β-amino-β-ethoxyacrylic acid ethyl ester and 1 g of p-toluenesulphonic acid in 200 ml of ethanol. After stirring overnight, the compound identified above, which had separated out as a precipitate, was filtered off and recrystallised from ethanol. Melting point: 143°, 15.2 g (26%).

EXAMPLE 39

3-Amino-1-(3-trifluoromethyl-4-chlorobenzyl)-pyrazol-5-one

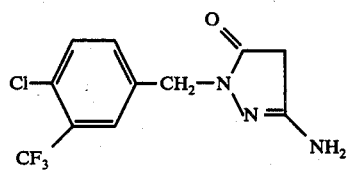

67 g of 4-chloro-3-trifluoromethylbenzylhydrazine were added dropwise, under nitrogen, to a solution of 46.1 g of β-amino-β-ethoxyacrylic acid ethyl ester and g of p-toluenesulphonic acid in 250 ml of ethanol. After stirring overnight, the solvent was distilled off in vacuo and the residue, which solidified, was filtered off and recrystallised from ethanol. The product was the compound identified above. Melting point: 132°, 25 g (30%).

EXAMPLE 40

3-Amino-1-(2-trifluoromethylbenzyl)-pyrazol-5-one

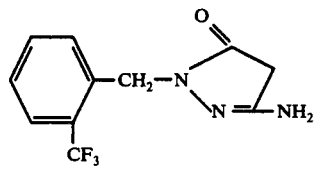

46 g of 2-trifluoromethylbenzylhydrazine were added dropwise, under nitrogen, to a solution of 38.2 g of β-amino-β-ethoxyacrylic acid ethyl ester and 2 g of p-toluenesulphonic acid in 250 ml of ethanol. After stirring overnight, the solvent was distilled off in vacuo and the residue was recrystallised from ethanol. The product was the compound identified above. Melting point: 184°, 22 g (34%).

EXAMPLE 41

3-Amino-1-(3-ethylbenzyl)-pyrazol-5-one

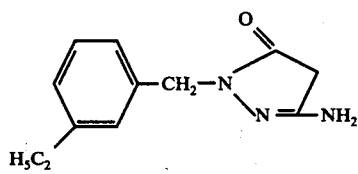

14.2 g of 3-ethylbenzylhydrazine were added dropwise to a solution of 15.1 g of β-amino-β-ethoxyacrylic acid ethyl ester and a pinch of p-toluenesulphonic acid in 80 ml of ethanol, in the course of which the temperature rose from 22° to 30°. After stirring overnight, the solvent was distilled off in vacuo and the solid residue was recrystallised from ethanol. The product was the compound identified above. Melting point: 73°, 5 g (24%).

EXAMPLE 42

3-Amino-1-(3-chloro-4-trifluoromethylbenzyl)-pyrazol-5-one

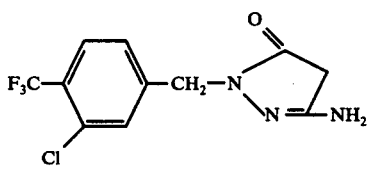

33 g of 3-chloro-4-trifluoromethylbenzylhydrazine were added dropwise, under nitrogen, to a solution of 23.5 g of β-amino-β-ethoxyacrylic acid ethyl ester and a pinch of p-toluenesulphonic acid in 100 ml of ethanol. After stirring overnight, the product which had precipitated was filtered off and recrystallised from ethanol. Melting point: 83°, 24 g (56%).

EXAMPLE 43

3-Amino-1-(3-trifluoromethyl-4-methylbenzyl)-pyrazol-5-one

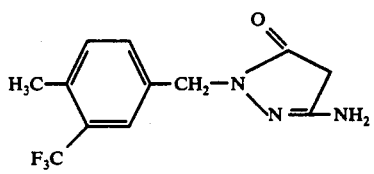

34 g of 4-methyl-3-trifluoromethylbenzylhydrazine were added dropwise, under nitrogen, to a solution of 26.5 g of β-amino-β-ethoxyacrylic acid ethyl ester and a pinch of p-toluenesulphonic acid in 100 ml of ethanol. After stirring overnight, the compound identified above, which had precipitated, was filtered off and recrystallised from ethanol. Melting point: 103°, 20 g (44%).

EXAMPLE 44:

3-Amino-1-(1,2-dichloronaphthyl-(7)-methyl)-pyrazol-5-one

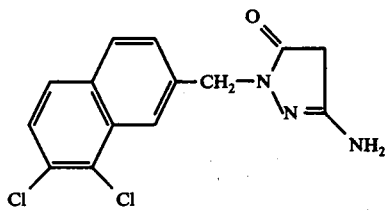

15.1 g of 1,2-dichloro-7-hydrazinomethyl-naphthalene were added, under nitrogen, to a solution of 10.3 g of β-amino-β-ethoxyacrylic acid ethyl ester and a pinch of p-toluenesulphonic acid in 100 ml of ethanol. After stirring overnight, the precipitate was filtered off and recrystallised from ethanol. The product was the compound identified above. Melting point: 200°, 4.7 g (23%).

EXAMPLE 45

3-Amino-1-(4-chlorobenzyl)-pyrazol-5-one

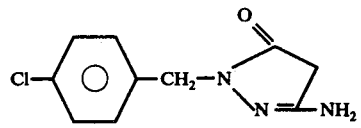

174 g (10%excess) of β-amino-β-ethoxyacrylic acid ethyl ester are introduced into 500 ml or ethanol. 156 g of 4-chlorobenzylhydrazine are added thereto while stirring. In the course thereof, the temperature rises to 30°–40°. The reaction mixture is stirred for a further 2 hours and is then left for 12 hours. Crystals which have separated out are filtered off, the solvent is driven off and the residue is taken up in water and rendered alkaline with 2 N NaOH. The aqueous alkaline phase is extracted with ether and the ether is discarded. The crystals already obtained from the reaction solution are dissolved in the phase containing sodium hydroxide and the solution is stirred for 30 minutes with animal charcoal and filtered. Introduction of $CO_2$ or acidification with dilute acetic acid yields the reaction product which is further purified by reprecipitating it once more or recrystallising it from alcohol. 138 g of the compound identified above as felted colorless needles of melting point 134° are obtained. (Yield: 62% of theory)

EXAMPLE 46

3-Amino-1-(3-chlorobenzyl)-pyrazol-5-one

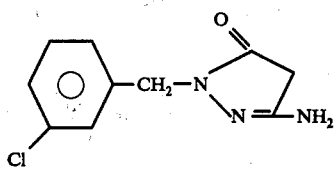

35 g (10% excess) of β-amino-β-ethoxyacrylic acid ethyl ester are introduced into 100 ml of ethanol. 32 g of 3-chlorobenzylhydrazine in 50 ml of ethanol are added while stirring. The mixture is worked up as above. 18.9 g of the compound identified above, as colorless felted needles of melting point 132°, are obtained. (Yield: 42% of theory)

EXAMPLE 47

3-Amino-1-(2-chlorobenzyl)-pyrazol-5-one

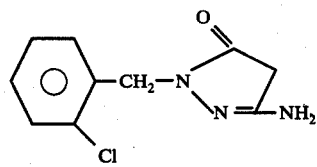

35 g of β-amino-β-ethoxyacrylic acid ethyl ester and 32 g of 2-chlorobenzylhydrazine when reacted as described in Example 45 yield 17.5 of the compound identified above as colorless crystals of melting point 153°. (Yield: 40% of theory)

EXAMPLE 48

3-Amino-1-(2,6-dichlorobenzyl)-pyrazol-5-one

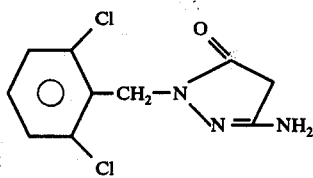

35 g of β-amino-β-ethoxyacrylic acid ethyl ester and 38 g of 2,6-dichlorobenzylhydrazine when reacted as described in Example 45, yield 24 g of the compound identified above as colorless crystals, corresponding to 46% of theory, of melting point 225°.

EXAMPLE 49

3-Amino-1-(3,4-dichlorobenzyl)-pyrazol-5-one

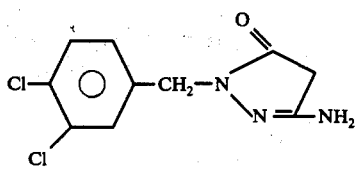

144 g (10% excess) of β-amino-β-methoxyacrylic acid methyl ester are introduced into 500 ml of dioxane. 191 g of 3,4-dichlorobenzylhydrazine are introduced into the reaction mixture while flushing with nitrogen. The mixture is stirred for 2 hours at 60°, the solvent is driven off on a rotary evaporator, the residue is worked with 600 ml of 2 N NaOH and extracted with ether, and the aqueous phase is stirred with animal charcoal for one-half hour. After filtration, the mixture is adjusted to pH 5 with dilute acetic acid. The product which initially is obtained as an oil becomes crystalline on rubbing and is finally purified by recrystallising it again from alcohol. 139 g, corresponding to about 54% of theory, of the compound identified above, as felted colorless needles of melting point 159° are obtained.

EXAMPLE 50:

3-Amino-1-(4-cyanobenzyl)-pyrazol-5-one

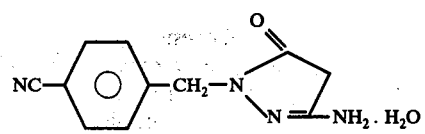

17.5 g of β-amino-β-ethoxyacrylic acid ethyl ester and 14.7 g of 4-cyanobenzylhydrazine yield, analogously to the procedure described in Example 45, 11.3 g, corresponding to 49% of theory, of colorless crystals which melt at 187° after drying in a drying tube. One reprecipitation or recrystallisation from aqueous solvents, the compound identified above crystallises with one mol of water of crystallisation.

EXAMPLE 51

3-Amino-1-(3-trifluoromethylbenzyl)-pyrazol-5-one

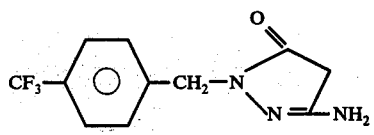

4.6 g of sodium are dissolved in 200 ml of ethanol. 42 g of β-amino-β-ethylmercaptoacrylic acid ethyl ester, as the hydrochloride, are introduced in the cold. 38 g of 4-trifluorobenzylhydrazine are then introduced into the mixture. The batch is stirred for 2 hours at 60° and is left to stand for 12 hours at room temperature. The solvent is distilled off, 200 ml of water and 200 ml of ether are added, the ether phase is separated off and the aqueous phase is acidified. The crude product is further purified by recrystallisation from alcohol. 33 g of the compound identified above, as felted needles of melting point 130°, corresponding to 63% of theory, are obtained.

EXAMPLE 52

3-Amino-1-(2,5-dichlorobenzyl)-pyrazol-5-one

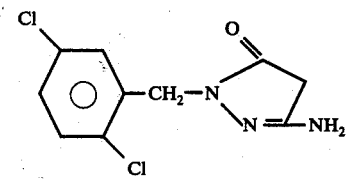

32.8 g of β-amino-β-ethoxyacrylic acid ethyl ester and 1 g of p-toluenesulphonic acid were dissolved in 120 ml of ethanol and 39 g of 2,5-dichlorobenzylhydrazine were added under nitrogen. After stirring for 2 hours the mixture was left to stand overnight and the compound identified above, which precipitated, was filtered off and recrystallised from ethanol. Melting point: 195°-196° C; Yield: 23 g (43%).

EXAMPLE 53

3-Amino-1-(3,5-dichlorobenzyl)-pyrazol-5-one

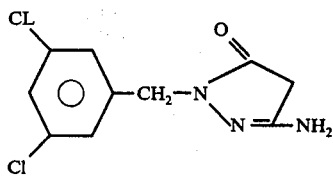

After adding 1 g of p-toluenesulphonic acid to a solution of 49.6 g of β-amino-β-ethoxyacrylic acid ethyl ester in 220 ml of ethanol, 59 g of 3,5-dichlorobenzylhydrazine were added dropwise under nitrogen. The solution was left to stand overnight and the solids which precipitated melted at 175°-176° after recrystallisation from ethanol. Yield: 40 g (48%) of the compound identified above.

EXAMPLE 54

3-Amino-1-(2,3-dichlorobenzyl)-pyrazol-5-one

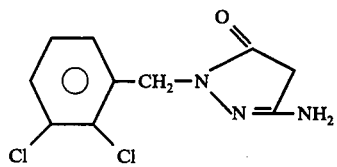

16.7 g of β-amino-β-ethoxyacrylic acid ethyl ester and 1 g of p-toluenesulphonic acid were dissolved in 100 ml of ethanol and 20.2 g of 2,3-dichlorobenzylhydrazine were added. After standing overnight at room temperature, the precipitate which had formed was filtered off and dissolved in 2 N sodium hydroxide solution. The alkaline solution was again extracted with ether and subsequently slightly acidified with dilute acetic acid. Hereupon the compound identified above precipitated and after recrystallisation from ethanol the melting point was 161°-162° C. Yield: 11 g (40%).

EXAMPLE 55

3-Amino-1-(3-trifluoromethylbenzyl)-pyrazol-5-one

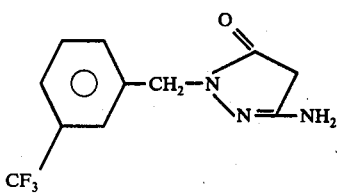

From 17.5 g of β-amino-β-ethoxyacrylic acid ethyl ester and 19 g of 3-trifluorobenzylhydrazine analogously to the procedure described in Example 45, 9 g of the compound identified above, as colorless crystals of melting point 144°, corresponding to 33% of theory, are obtained.

EXAMPLE 56

3-Amino-1-(4-methoxybenzyl)-pyrazol-5-one

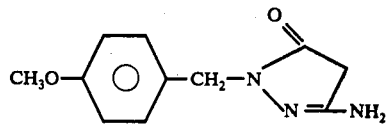

From 17.5 g of β-amino-β-ethoxyacrylic acid ethyl ester and 15.2 g of 4-methoxybenzylhydrazine, analogously to the procedure described in Example 45, 9.7 g of the compound identified above, as colorless crystals of melting point 161°, corresponding to 44% of theory, are obtained.

EXAMPLE 57

3-Amino-1-(2,4-dichlorobenzyl)-pyrazol-5-one

3-Amino-1-(2,4-dichlorobenzyl)-pyrazol-5-one

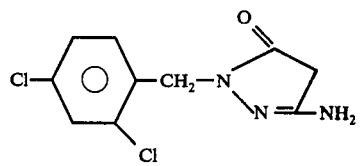

From 17.5 g of β-amino-β-ethoxyacrylic acid ethyl ester and 20.2 g of 2,4-dichlorobenzylhydrazine analogously to the procedure described in Example 45, 11 g of the compound identified above, as colorless crystals of melting point 189°, corresponding to 40% of theory, are obtained.

EXAMPLE 58

3-Amino-1-(naphthyl-(1)-methyl)-pyrazol-5-one

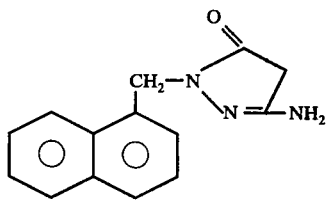

37.5 g of β-amino-β-ethoxyacrylic acid ethyl ester and 40.5 g of β-hydrazinomethyl-naphthalene yield, analogously to the procedure described in Example 45, 24 g of the compound identified above, as colorless crystals of melting point 180°, corresponding to 50% of theory.

What is claimed is:
1. A compound of the formula

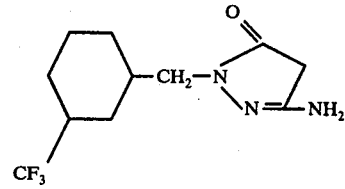

or a pharmaceutically acceptable non-toxic salt thereof wherein
R is (a) naphthyl having 1 or 2 identical or different substituents selected from the group consisting of halogen and alkyl of 1 to 4 carbon atoms; or
(b) unsubstituted β-naphthyl.

2. A compound according to claim 1 wherein R is naphthyl having 1 or 2 identical substituents selected from the group consisting of halogen and alkyl of 1 to 4 carbon atoms.

3. A compound according to claim 1 wherein R is β-naphthyl.

4. The compound according to claim 1 which is

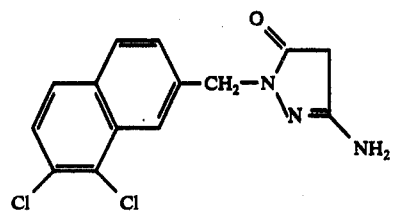

UNITED STATES PATENT AND TRADEMARK OFFICE
CERTIFICATE OF CORRECTION

PATENT NO. : 4,076,943
DATED : February 28, 1978
INVENTOR(S) : HARALD HORSTMANN ET AL It is certified that error appears in the above-identified patent and that said Letters Patent are hereby corrected as shown below:

The structural formula in
Claim 1 should read as follows:

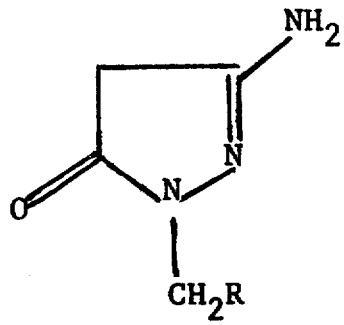

Signed and Sealed this

Seventh Day of November 1978

[SEAL]

Attest:

RUTH C. MASON
Attesting Officer

DONALD W. BANNER
Commissioner of Patents and Trademarks